US010183979B2

(12) United States Patent
Alvarez et al.

(10) Patent No.: US 10,183,979 B2
(45) Date of Patent: *Jan. 22, 2019

(54) FUSION POLYPEPTIDES COMPRISING MUCIN-DOMAIN POLYPEPTIDE LINKERS

(71) Applicant: Alkermes, Inc., Waltham, MA (US)

(72) Inventors: Juan Alvarez, Chelmsford, MA (US); Leslie A. McSweeney, Milford, MA (US)

(73) Assignee: Alkermes, Inc., Waltham, MA (US)

( * ) Notice: Subject to any disclaimer, the term of this patent is extended or adjusted under 35 U.S.C. 154(b) by 213 days.

This patent is subject to a terminal disclaimer.

(21) Appl. No.: 15/044,310

(22) Filed: Feb. 16, 2016

(65) Prior Publication Data

US 2016/0237132 A1     Aug. 18, 2016

Related U.S. Application Data

(62) Division of application No. 13/911,834, filed on Jun. 6, 2013, now Pat. No. 9,296,801.

(60) Provisional application No. 61/778,812, filed on Mar. 13, 2013, provisional application No. 61/657,264, filed on Jun. 8, 2012, provisional application No. 61/657,285, filed on Jun. 8, 2012, provisional application No. 61/778,575, filed on Mar. 13, 2013, provisional application No. 61/657,378, filed on Jun. 8, 2012, provisional application No. 61/723,081, filed on Nov. 6, 2012.

(51) Int. Cl.

| | |
|---|---|
| C07K 14/435 | (2006.01) |
| C07K 14/55 | (2006.01) |
| C07K 14/47 | (2006.01) |
| C07K 14/545 | (2006.01) |
| C07K 14/54 | (2006.01) |
| C07K 14/715 | (2006.01) |
| C07K 14/50 | (2006.01) |
| C07K 14/705 | (2006.01) |
| C07K 14/71 | (2006.01) |
| C07K 14/575 | (2006.01) |
| A61K 38/00 | (2006.01) |
| A61K 39/00 | (2006.01) |

(52) U.S. Cl.
CPC .......... *C07K 14/55* (2013.01); *C07K 14/4713* (2013.01); *C07K 14/4727* (2013.01); *C07K 14/50* (2013.01); *C07K 14/54* (2013.01); *C07K 14/545* (2013.01); *C07K 14/5412* (2013.01); *C07K 14/5443* (2013.01); *C07K 14/57563* (2013.01); *C07K 14/70503* (2013.01); *C07K 14/71* (2013.01); *C07K 14/7155* (2013.01); *A61K 38/00* (2013.01); *A61K 2039/505* (2013.01); *C07K 2319/00* (2013.01); *C07K 2319/02* (2013.01); *C07K 2319/30* (2013.01); *C07K 2319/31* (2013.01); *C07K 2319/74* (2013.01); *C07K 2319/91* (2013.01)

(58) Field of Classification Search
None
See application file for complete search history.

(56) References Cited

U.S. PATENT DOCUMENTS

| | | | |
|---|---|---|---|
| 2005/0260222 A1 | 11/2005 | Gupta et al. | |
| 2005/0265995 A1 | 12/2005 | Tomlinson et al. | |
| 2017/0233447 A1* | 8/2017 | Qin ..................... | C07K 14/545 424/85.2 |

FOREIGN PATENT DOCUMENTS

| | | |
|---|---|---|
| JP | 2003513656 A | 4/2003 |
| JP | 2003514552 A | 4/2003 |
| JP | 2004528014 A | 9/2004 |
| JP | 2006517191 A | 7/2006 |
| JP | 2008521489 A | 6/2008 |
| JP | 2010536341 A | 12/2010 |
| WO | 2002062375 A1 | 8/2002 |
| WO | 2005034863 A2 | 4/2005 |
| WO | 2007020889 A1 | 2/2007 |
| WO | 2007063907 A1 | 6/2007 |
| WO | 2009153960 A1 | 12/2009 |
| WO | 2010127029 A1 | 11/2010 |

OTHER PUBLICATIONS

Nomellini, J.F., et al., "S-Layer-Mediated Display of the Immunoglobulin G-Binding Domain of Streptococcal Protein G on the Surface of Caulobacter crescentus: Development of an Immunoactive Reagent," Applied and Environmental Microbiology, 73(10): pp. 3245-3253 (May 2007).

(Continued)

*Primary Examiner* — Michael Pak
(74) *Attorney, Agent, or Firm* — Elmore Patent Law Group, P.C.; Darlene Vanstone; Carolyn Elmore

(57) ABSTRACT

The invention provides fusion proteins having improved bioactivity comprising a first polypeptide fusion partner and a second polypeptide fusion partner wherein the first fusion partner is linked to the second fusion partner by a mucin-domain polypeptide linker and wherein the bioactivity of the fusion protein of the invention is improved as compared to fusion of the first polypeptide fusion partner and the second polypeptide fusion partner in the absence of the mucin-domain polypeptide linker. Mucin-domain polypeptide linkers comprise a mucin domain that is rich in potential glycosylation sites, and has a high content of serine and/or threonine and proline, which can represent greater than 40% of the amino acids within the mucin domain and further comprise at least about 60% of its mass due to the glycans.

7 Claims, 7 Drawing Sheets

Specification includes a Sequence Listing.

(56) References Cited

OTHER PUBLICATIONS

Fontenot, D., et al., "Human Immunodeficiency Virus (HIV) antigens: Structure and Serology of Multivalent Human Mucin MUC1-HIV V3 Chimeric Proteins," Proc. Natl. Acad. Sci. USA, vol. 92, pp. 315-319 (Jan. 1995).

Shen, H., et al., "Deletion of the Linker Connecting the Catalytic and Cellulose-Binding Domains of Endoglucanase A (CenA) of Cellulomonas fimi Alters Its Conformation and Catalytic Activity," The Journal of Biological Chemistry, 266(17): pp. 11335-11340 (1991).

Chen, X., et al., "Fusion Protein Linkers: Property, Design and Functionality," Advanced Drug Delivery Reviews 65: pp. 1357-1369 (2012).

Publications Related to P18510-IL1RA Human, www.uniprot.org.

* cited by examiner

SEQUENCE LISTING

<160> NUMBER OF SEQ ID NOS: 23

<210> SEQ ID NO 1
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Ala Met Lys Arg Gly Leu Cys Cys Val Leu Leu Cys Gly
1               5                   10                  15

Ala Val Phe Val Ser Ala Arg Arg Pro Ser Gly Arg Lys Ser Ser Lys
            20                  25                  30

Met Gln Ala Phe Arg Ile Trp Asp Val Asn Gln Lys Thr Phe Tyr Leu
        35                  40                  45

Arg Asn Asn Gln Leu Val Ala Gly Tyr Leu Gln Gly Pro Asn Val Asn
    50                  55                  60

Leu Glu Glu Lys Ile Asp Val Val Pro Ile Glu Pro His Ala Leu Phe
65                  70                  75                  80

Leu Gly Ile His Gly Gly Lys Met Cys Leu Ser Cys Val Lys Ser Gly
                85                  90                  95

Asp Glu Thr Arg Leu Gln Leu Glu Ala Val Asn Ile Thr Asp Leu Ser
            100                 105                 110

Glu Asn Arg Lys Gln Asp Lys Arg Phe Ala Phe Ile Arg Ser Asp Ser
        115                 120                 125

Gly Pro Thr Thr Ser Phe Glu Ser Ala Ala Cys Pro Gly Trp Phe Leu
    130                 135                 140

Cys Thr Ala Met Glu Ala Asp Gln Pro Val Ser Leu Thr Asn Met Pro
145                 150                 155                 160

Asp Glu Gly Val Met Val Thr Lys Phe Tyr Phe Gln Glu Asp Glu Thr
                165                 170                 175

Gly Gly Gly Thr His Thr Cys Pro Pro Cys Pro Ala Pro Glu Leu Leu
            180                 185                 190

-continued

```
Gly Gly Pro Ser Val Phe Leu Phe Pro Pro Lys Pro Lys Asp Thr Leu
            195                 200                 205

Met Ile Ser Arg Thr Pro Glu Val Thr Cys Val Val Val Asp Val Ser
    210                 215                 220

His Glu Asp Pro Glu Val Lys Phe Asn Trp Tyr Val Asp Gly Val Glu
225                 230                 235                 240

Val His Asn Ala Lys Thr Lys Pro Arg Glu Glu Gln Tyr Asn Ser Thr
                245                 250                 255

Tyr Arg Val Val Ser Val Leu Thr Val Leu His Gln Asp Trp Leu Asn
            260                 265                 270

Gly Lys Glu Tyr Lys Cys Lys Val Ser Asn Lys Ala Leu Pro Ala Pro
        275                 280                 285

Ile Glu Lys Thr Ile Ser Lys Ala Lys Gly Gln Pro Arg Glu Pro Gln
    290                 295                 300

Val Tyr Thr Leu Pro Pro Ser Arg Glu Glu Met Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
            340                 345                 350

Pro Val Leu Asp Ser Asp Gly Ser Phe Phe Leu Tyr Ser Lys Leu Thr
        355                 360                 365

Val Asp Lys Ser Arg Trp Gln Gln Gly Asn Val Phe Ser Cys Ser Val
    370                 375                 380

Met His Glu Ala Leu His Asn His Tyr Thr Gln Lys Ser Leu Ser Leu
385                 390                 395                 400

Ser Pro Gly Lys

<210> SEQ ID NO 2
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Ala Met Lys Arg Gly Leu Cys Cys Val Leu Leu Leu Cys Gly
1               5                   10                  15

Ala Val Phe Val Ser Ala Arg Arg Pro Ser Gly Arg Lys Ser Ser Lys
            20                  25                  30

Met Gln Ala Phe Arg Ile Trp Asp Val Asn Gln Lys Thr Phe Tyr Leu
        35                  40                  45

Arg Asn Asn Gln Leu Val Ala Gly Tyr Leu Gln Gly Pro Asn Val Asn
    50                  55                  60

Leu Glu Glu Lys Ile Asp Val Val Pro Ile Glu Pro His Ala Leu Phe
65                  70                  75                  80

Leu Gly Ile His Gly Gly Lys Met Cys Leu Ser Cys Val Lys Ser Gly
                85                  90                  95

Asp Glu Thr Arg Leu Gln Leu Glu Ala Val Asn Ile Thr Asp Leu Ser
            100                 105                 110

Glu Asn Arg Lys Gln Asp Lys Arg Phe Ala Phe Ile Arg Ser Asp Ser
        115                 120                 125

Gly Pro Thr Thr Ser Phe Glu Ser Ala Ala Cys Pro Gly Trp Phe Leu
    130                 135                 140
```

```
Cys Thr Ala Met Glu Ala Asp Gln Pro Val Ser Leu Thr Asn Met Pro
145                 150                 155                 160

Asp Glu Gly Val Met Val Thr Lys Phe Tyr Phe Gln Glu Asp Glu Ser
                165                 170                 175

Gly Ser Gly Gly Ala Ser Ser Glu Ser Ser Ala Ser Ser Asp Gly Pro
            180                 185                 190

His Pro Val Ile Thr Glu Ser Arg Ala Ser Ser Glu Ser Ser Ala Ser
        195                 200                 205

Ser Asp Gly Pro His Pro Val Ile Thr Glu Ser Arg Glu Pro Lys Ser
    210                 215                 220

Ser Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 3
<211> LENGTH: 545
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asp Ala Met Lys Arg Gly Leu Cys Cys Val Leu Leu Leu Cys Gly
1               5                   10                  15

Ala Val Phe Val Ser Ala Arg Leu Leu Asp Pro Cys Gly Tyr Ile Ser
                20                  25                  30

Pro Glu Ser Pro Val Val Gln Leu His Ser Asn Phe Thr Ala Val Cys
                35                  40                  45
```

```
Val Leu Lys Glu Lys Cys Met Asp Tyr Phe His Val Asn Ala Asn Tyr
     50                  55                  60

Ile Val Trp Lys Thr Asn His Phe Thr Ile Pro Lys Glu Gln Tyr Thr
 65              70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
                100                 105                 110

Gln Asn Val Tyr Gly Ile Thr Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
    275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Thr Gly Gly Gly Pro Cys Pro Ala Pro Glu Leu Leu Gly Gly Pro
                325                 330                 335

Ser Val Phe Leu Phe Pro Pro Lys Pro Lys Asp Thr Leu Met Ile Ser
            340                 345                 350

Arg Thr Pro Glu Val Thr Cys Val Val Asp Val Ser His Glu Asp
    355                 360                 365

Pro Glu Val Lys Phe Asn Trp Tyr Val Asp Gly Val Glu Val His Asn
    370                 375                 380

Ala Lys Thr Lys Pro Arg Glu Glu Gln Tyr Asn Ser Thr Tyr Arg Val
385                 390                 395                 400

Val Ser Val Leu Thr Val Leu His Gln Asp Trp Leu Asn Gly Lys Glu
                405                 410                 415

Tyr Lys Cys Lys Val Ser Asn Lys Ala Leu Pro Ala Pro Ile Glu Lys
            420                 425                 430

Thr Ile Ser Lys Ala Lys Gly Gln Pro Arg Glu Pro Gln Val Tyr Thr
        435                 440                 445

Leu Pro Pro Ser Arg Glu Glu Met Thr Lys Asn Gln Val Ser Leu Thr
450                 455                 460
```

```
Cys Leu Val Lys Gly Phe Tyr Pro Ser Asp Ile Ala Val Glu Trp Glu
465                 470                 475                 480

Ser Asn Gly Gln Pro Glu Asn Asn Tyr Lys Thr Thr Pro Pro Val Leu
            485                 490                 495

Asp Ser Asp Gly Ser Phe Phe Leu Tyr Ser Lys Leu Thr Val Asp Lys
                500                 505                 510

Ser Arg Trp Gln Gln Gly Asn Val Phe Ser Cys Ser Val Met His Glu
        515                 520                 525

Ala Leu His Asn His Tyr Thr Gln Lys Ser Leu Ser Leu Ser Pro Gly
    530                 535                 540

Lys
545

<210> SEQ ID NO 4
<211> LENGTH: 601
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Tyr Arg Met Gln Leu Leu Ser Cys Ile Ala Leu Ser Leu Ala Leu
1               5                   10                  15

Val Thr Asn Ser Leu Leu Asp Pro Cys Gly Tyr Ile Ser Pro Glu Ser
            20                  25                  30

Pro Val Val Gln Leu His Ser Asn Phe Thr Ala Val Cys Val Leu Lys
        35                  40                  45

Glu Lys Cys Met Asp Tyr Phe His Val Asn Ala Asn Tyr Ile Val Trp
50                  55                  60

Lys Thr Asn His Phe Thr Ile Pro Lys Glu Gln Tyr Thr Ile Ile Asn
65                  70                  75                  80

Arg Thr Ala Ser Ser Val Thr Phe Thr Asp Ile Ala Ser Leu Asn Ile
                85                  90                  95

Gln Leu Thr Cys Asn Ile Leu Thr Phe Gly Gln Leu Glu Gln Asn Val
            100                 105                 110

Tyr Gly Ile Thr Ile Ile Ser Gly Leu Pro Pro Glu Lys Pro Lys Asn
        115                 120                 125

Leu Ser Cys Ile Val Asn Glu Gly Lys Lys Met Arg Cys Glu Trp Asp
    130                 135                 140

Gly Gly Arg Glu Thr His Leu Glu Thr Asn Phe Thr Leu Lys Ser Glu
145                 150                 155                 160

Trp Ala Thr His Lys Phe Ala Asp Cys Lys Ala Lys Arg Asp Thr Pro
                165                 170                 175

Thr Ser Cys Thr Val Asp Tyr Ser Thr Val Tyr Phe Val Asn Ile Glu
            180                 185                 190

Val Trp Val Glu Ala Glu Asn Ala Leu Gly Lys Val Thr Ser Asp His
        195                 200                 205

Ile Asn Phe Asp Pro Val Tyr Lys Val Lys Pro Asn Pro Pro His Asn
    210                 215                 220

Leu Ser Val Ile Asn Ser Glu Glu Leu Ser Ile Leu Lys Leu Thr Trp
225                 230                 235                 240

Thr Asn Pro Ser Ile Lys Ser Val Ile Ile Leu Lys Tyr Asn Ile Gln
                245                 250                 255

Tyr Arg Thr Lys Asp Ala Ser Thr Trp Ser Gln Ile Pro Pro Glu
            260                 265                 270
```

Asp Thr Ala Ser Thr Arg Ser Ser Phe Thr Val Gln Asp Leu Lys Pro
             275                 280                 285

Phe Thr Glu Tyr Val Phe Arg Ile Arg Cys Met Lys Glu Asp Gly Lys
290                 295                 300

Gly Tyr Trp Ser Asp Trp Ser Glu Glu Ala Ser Gly Ile Thr Tyr Glu
305                 310                 315                 320

Asp Arg Gly Gly Gly Ser Gly Gly Ala Ser Ser Glu Ser Ser Ala
                 325                 330                 335

Ser Ser Asp Gly Pro His Pro Val Ile Thr Glu Ser Arg Ala Ser Ser
             340                 345                 350

Glu Ser Ser Ala Ser Ser Asp Gly Pro His Pro Val Ile Thr Glu Ser
             355                 360                 365

Arg Glu Pro Lys Ser Ser Asp Lys Thr His Thr Cys Pro Pro Cys Pro
370                 375                 380

Ala Pro Glu Leu Leu Gly Gly Pro Ser Val Phe Leu Phe Pro Pro Lys
385                 390                 395                 400

Pro Lys Asp Thr Leu Met Ile Ser Arg Thr Pro Glu Val Thr Cys Val
             405                 410                 415

Val Val Asp Val Ser His Glu Asp Pro Glu Val Lys Phe Asn Trp Tyr
             420                 425                 430

Val Asp Gly Val Glu Val His Asn Ala Lys Thr Lys Pro Arg Glu Glu
             435                 440                 445

Gln Tyr Asn Ser Thr Tyr Arg Val Val Ser Val Leu Thr Val Leu His
             450                 455                 460

Gln Asp Trp Leu Asn Gly Lys Glu Tyr Lys Cys Lys Val Ser Asn Lys
465                 470                 475                 480

Ala Leu Pro Ala Pro Ile Glu Lys Thr Ile Ser Lys Ala Lys Gly Gln
             485                 490                 495

Pro Arg Glu Pro Gln Val Tyr Thr Leu Pro Pro Ser Arg Glu Glu Met
             500                 505                 510

Thr Lys Asn Gln Val Ser Leu Thr Cys Leu Val Lys Gly Phe Tyr Pro
             515                 520                 525

Ser Asp Ile Ala Val Glu Trp Glu Ser Asn Gly Gln Pro Glu Asn Asn
             530                 535                 540

Tyr Lys Thr Thr Pro Pro Val Leu Asp Ser Asp Gly Ser Phe Phe Leu
545                 550                 555                 560

Tyr Ser Lys Leu Thr Val Asp Lys Ser Arg Trp Gln Gln Gly Asn Val
             565                 570                 575

Phe Ser Cys Ser Val Met His Glu Ala Leu His Asn His Tyr Thr Gln
             580                 585                 590

Lys Ser Leu Ser Leu Ser Pro Gly Lys
             595                 600

<210> SEQ ID NO 5
<211> LENGTH: 20
<212> TYPE: PRT
<213> ORGANISM: Homo sapiens

<400> SEQUENCE: 5

Pro Ala Pro Gly Ser Thr Ala Pro Ala His Gly Val Thr Ser Ala
1               5                   10                  15

Pro Asp Thr Arg
             20

```
<210> SEQ ID NO 6
<211> LENGTH: 23
<212> TYPE: PRT
<213> ORGANISM: Homo sapiens

<400> SEQUENCE: 6

Ile Thr Thr Thr Thr Thr Val Thr Pro Thr Pro Thr Pro Thr Gly Thr
1               5                   10                  15

Gln Thr Pro Thr Thr Thr Pro
            20

<210> SEQ ID NO 7
<211> LENGTH: 17
<212> TYPE: PRT
<213> ORGANISM: Homo sapiens

<400> SEQUENCE: 7

Ile Thr Thr Thr Glu Thr Thr Ser His Asp Thr Pro Ser Phe Thr Ser
1               5                   10                  15

Ser

<210> SEQ ID NO 8
<211> LENGTH: 16
<212> TYPE: PRT
<213> ORGANISM: Homo sapiens

<400> SEQUENCE: 8

Ala Thr Pro Leu Pro Val Thr Asp Thr Ser Ser Ala Ser Thr Gly His
1               5                   10                  15

<210> SEQ ID NO 9
<211> LENGTH: 8
<212> TYPE: PRT
<213> ORGANISM: Homo sapiens

<400> SEQUENCE: 9

Thr Thr Ser Thr Thr Ser Ala Pro
1               5

<210> SEQ ID NO 10
<211> LENGTH: 29
<212> TYPE: PRT
<213> ORGANISM: Homo sapiens

<400> SEQUENCE: 10

Ala Thr Gly Ser Thr Ala Thr Pro Ser Ser Thr Pro Gly Thr Thr His
1               5                   10                  15

Thr Pro Pro Val Leu Thr Thr Thr Ala Thr Thr Pro Thr
            20                  25

<210> SEQ ID NO 11
<211> LENGTH: 23
<212> TYPE: PRT
<213> ORGANISM: Homo sapiens

<400> SEQUENCE: 11

Thr Thr Ala Ala Pro Pro Thr Pro Ser Ala Thr Thr Gln Ala Pro Pro
1               5                   10                  15

Ser Ser Ser Ala Pro Pro Glu
            20

<210> SEQ ID NO 12
<211> LENGTH: 19
```

```
<212> TYPE: PRT
<213> ORGANISM: Homo sapiens

<400> SEQUENCE: 12

Glu Glu Ser Thr Thr Val His Ser Ser Pro Gly Ala Thr Gly Thr Ala
1               5                   10                  15

Leu Phe Pro

<210> SEQ ID NO 13
<211> LENGTH: 59
<212> TYPE: PRT
<213> ORGANISM: Homo sapiens

<400> SEQUENCE: 13

Ser Ser Ser Pro Thr Pro Ala Glu Gly Thr Ser Met Pro Thr Ser Thr
1               5                   10                  15

Tyr Ser Glu Gly Arg Thr Pro Leu Thr Ser Met Pro Val Ser Thr Thr
                20                  25                  30

Leu Val Ala Thr Ser Ala Ile Ser Thr Leu Ser Thr Thr Pro Val Asp
            35                  40                  45

Thr Ser Thr Pro Val Thr Asn Ser Thr Glu Ala
        50                  55

<210> SEQ ID NO 14
<211> LENGTH: 19
<212> TYPE: PRT
<213> ORGANISM: Homo sapiens

<400> SEQUENCE: 14

Ser Glu Ser Ser Ala Ser Ser Asp Gly Pro His Pro Val Ile Thr Pro
1               5                   10                  15

Ser Arg Ala

<210> SEQ ID NO 15
<211> LENGTH: 15
<212> TYPE: PRT
<213> ORGANISM: Homo sapiens

<400> SEQUENCE: 15

Ala Thr Asn Ser Glu Ser Ser Thr Val Ser Ser Gly Ile Ser Thr
1               5                   10                  15

<210> SEQ ID NO 16
<211> LENGTH: 6
<212> TYPE: PRT
<213> ORGANISM: Homo sapiens

<400> SEQUENCE: 16

Val Pro Thr Thr Thr Thr
1               5

<210> SEQ ID NO 17
<211> LENGTH: 10
<212> TYPE: PRT
<213> ORGANISM: Homo sapiens

<400> SEQUENCE: 17

Gln Thr Thr Gln Pro Ala Ala Thr Glu Ala
1               5                   10

<210> SEQ ID NO 18
<211> LENGTH: 503
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Asn Gln Trp Leu Gln Asp Met Thr Thr His Leu Ile Leu Arg Ser
1               5                   10                  15

Phe Lys Glu Phe Leu Gln Ser Ser Leu Arg Ala Leu Arg Gln Met Ser
            20                  25                  30

Gly Gly Ser Gly Gly Gly Ser Ser Glu Arg Ile Asp Lys Gln Ile Arg
        35                  40                  45

Tyr Ile Leu Asp Gly Ile Ser Ala Leu Arg Lys Glu Thr Cys Asn Lys
    50                  55                  60

Ser Asn Met Cys Glu Ser Ser Lys Glu Ala Leu Ala Glu Asn Asn Leu
65                  70                  75                  80

Asn Leu Pro Lys Met Ala Glu Lys Asp Gly Cys Phe Gln Ser Gly Phe
                85                  90                  95

Asn Glu Glu Thr Cys Leu Val Lys Ile Ile Thr Gly Leu Leu Glu Phe
            100                 105                 110

Glu Val Tyr Leu Glu Tyr Leu Gln Asn Arg Phe Glu Ser Ser Glu Glu
        115                 120                 125

Gln Ala Arg Ala Val Gln Met Ser Thr Lys Val Leu Ile Gln Phe Leu
    130                 135                 140

Gln Lys Lys Ala Lys Asn Leu Asp Ala Ile Thr Thr Pro Asp Pro Thr
145                 150                 155                 160

Thr Asn Ala Ser Leu Leu Thr Lys Leu Gln Ala Ser Glu Leu Leu Asp
                165                 170                 175

Pro Cys Gly Tyr Ile Ser Pro Glu Ser Pro Val Val Gln Leu His Ser
            180                 185                 190

Asn Phe Thr Ala Val Cys Val Leu Lys Glu Lys Cys Met Asp Tyr Phe
        195                 200                 205

His Val Asn Ala Asn Tyr Ile Val Trp Lys Thr Asn His Phe Thr Ile
    210                 215                 220

Pro Lys Glu Gln Tyr Thr Ile Ile Asn Arg Thr Ala Ser Ser Val Thr
225                 230                 235                 240

Phe Thr Asp Ile Ala Ser Leu Asn Ile Gln Leu Thr Cys Asn Ile Leu
                245                 250                 255

Thr Phe Gly Gln Leu Glu Gln Asn Val Tyr Gly Ile Thr Ile Ile Ser
            260                 265                 270

Gly Gly Ser Glu Arg Lys Cys Cys Val Glu Cys Pro Pro Cys Pro Ala
        275                 280                 285

Pro Pro Val Ala Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Gln Phe Asn Trp Tyr Val Asp
                325                 330                 335

Gly Val Glu Val His Asn Ala Lys Thr Lys Pro Arg Glu Glu Gln Phe
            340                 345                 350

Asn Ser Thr Phe Arg Val Val Ser Val Leu Thr Val Val His Gln Asp
        355                 360                 365

Trp Leu Asn Gly Lys Glu Tyr Lys Cys Lys Val Ser Asn Lys Gly Leu
    370                 375                 380
```

```
Pro Ala Pro Ile Glu Lys Thr Ile Ser Lys Thr Lys Gly Gln Pro Arg
385                 390                 395                 400

Glu Pro Gln Val Tyr Thr Leu Pro Pro Ser Arg Glu Glu Met Thr Lys
            405                 410                 415

Asn Gln Val Ser Leu Thr Cys Leu Val Lys Gly Phe Tyr Pro Ser Asp
            420                 425                 430

Ile Ser Val Glu Trp Glu Ser Asn Gly Gln Pro Glu Asn Asn Tyr Lys
        435                 440                 445

Thr Thr Pro Pro Met Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
            485                 490                 495

Leu Ser Leu Ser Pro Gly Lys
            500

<210> SEQ ID NO 19
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Asn Gln Trp Leu Gln Asp Met Thr Thr His Leu Ile Leu Arg Ser
1               5                   10                  15

Phe Lys Glu Phe Leu Gln Ser Ser Leu Arg Ala Leu Arg Gln Met Ser
            20                  25                  30

Gly Gly Ser Gly Gly Gly Ser Ser Glu Arg Ile Asp Lys Gln Ile Arg
        35                  40                  45

Tyr Ile Leu Asp Gly Ile Ser Ala Leu Arg Lys Glu Thr Cys Asn Lys
    50                  55                  60

Ser Asn Met Cys Glu Ser Ser Lys Glu Ala Leu Ala Glu Asn Asn Leu
65                  70                  75                  80

Asn Leu Pro Lys Met Ala Glu Lys Asp Gly Cys Phe Gln Ser Gly Phe
                85                  90                  95

Asn Glu Glu Thr Cys Leu Val Lys Ile Ile Thr Gly Leu Leu Glu Phe
            100                 105                 110

Glu Val Tyr Leu Glu Tyr Leu Gln Asn Arg Phe Glu Ser Ser Glu Glu
        115                 120                 125

Gln Ala Arg Ala Val Gln Met Ser Thr Lys Val Leu Ile Gln Phe Leu
    130                 135                 140

Gln Lys Lys Ala Lys Asn Leu Asp Ala Ile Thr Thr Pro Asp Pro Thr
145                 150                 155                 160

Thr Asn Ala Ser Leu Leu Thr Lys Leu Gln Ala Ser Glu Leu Leu Asp
                165                 170                 175

Pro Cys Gly Tyr Ile Ser Pro Glu Ser Pro Val Val Gln Leu His Ser
            180                 185                 190

Asn Phe Thr Ala Val Cys Val Leu Lys Glu Lys Cys Met Asp Tyr Phe
        195                 200                 205

His Val Asn Ala Asn Tyr Ile Val Trp Lys Thr Asn His Phe Thr Ile
    210                 215                 220

Pro Lys Glu Gln Tyr Thr Ile Ile Asn Arg Thr Ala Ser Ser Val Thr
```

```
                225                 230                 235                 240
        Phe Thr Asp Ile Ala Ser Leu Asn Ile Gln Leu Thr Cys Asn Ile Leu
                            245                 250                 255
        Thr Phe Gly Gln Leu Glu Gln Asn Val Tyr Gly Ile Thr Ile Ile Ser
                    260                 265                 270
        Gly Gly Gly Gly Ser Ala Ser Glu Ser Ser Ala Ser Ser Asp
                    275                 280                 285
        Gly Pro His Pro Val Ile Thr Glu Ser Arg Ala Ser Ser Glu Ser Ser
                    290                 295                 300
        Ala Ser Ser Asp Gly Pro His Pro Val Ile Thr Glu Ser Arg Ser Glu
        305                 310                 315                 320
        Arg Lys Cys Cys Val Glu Cys Pro Pro Cys Pro Ala Pro Pro Val Ala
                            325                 330                 335
        Gly Pro Ser Val Phe Leu Phe Pro Pro Lys Pro Lys Asp Thr Leu Met
                    340                 345                 350
        Ile Ser Arg Thr Pro Glu Val Thr Cys Val Val Val Asp Val Ser His
                    355                 360                 365
        Glu Asp Pro Glu Val Gln Phe Asn Trp Tyr Val Asp Gly Val Glu Val
                    370                 375                 380
        His Asn Ala Lys Thr Lys Pro Arg Glu Glu Gln Phe Asn Ser Thr Phe
        385                 390                 395                 400
        Arg Val Val Ser Val Leu Thr Val Val His Gln Asp Trp Leu Asn Gly
                            405                 410                 415
        Lys Glu Tyr Lys Cys Lys Val Ser Asn Lys Gly Leu Pro Ala Pro Ile
                    420                 425                 430
        Glu Lys Thr Ile Ser Lys Thr Lys Gly Gln Pro Arg Glu Pro Gln Val
                    435                 440                 445
        Tyr Thr Leu Pro Pro Ser Arg Glu Glu Met Thr Lys Asn Gln Val Ser
                    450                 455                 460
        Leu Thr Cys Leu Val Lys Gly Phe Tyr Pro Ser Asp Ile Ser Val Glu
        465                 470                 475                 480
        Trp Glu Ser Asn Gly Gln Pro Glu Asn Asn Tyr Lys Thr Thr Pro Pro
                            485                 490                 495
        Met Leu Asp Ser Asp Gly Ser Phe Phe Leu Tyr Ser Lys Leu Thr Val
                    500                 505                 510
        Asp Lys Ser Arg Trp Gln Gln Gly Asn Val Phe Ser Cys Ser Val Met
                    515                 520                 525
        His Glu Ala Leu His Asn His Tyr Thr Gln Lys Ser Leu Ser Leu Ser
        530                 535                 540
        Pro Gly Lys
        545

<210> SEQ ID NO 20
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Arg Pro Ser Gly Arg Lys Ser Ser Lys Met Gln Ala Phe Arg Ile Trp
        1               5                   10                  15
        Asp Val Asn Gln Lys Thr Phe Tyr Leu Arg Asn Asn Gln Leu Val Ala
                    20                  25                  30
```

Gly Tyr Leu Gln Gly Pro Asn Val Asn Leu Glu Lys Ile Asp Val
           35                  40                  45

Val Pro Ile Glu Pro His Ala Leu Phe Leu Gly Ile His Gly Gly Lys
 50                  55                  60

Met Cys Leu Ser Cys Val Lys Ser Gly Asp Glu Thr Arg Leu Gln Leu
 65                  70                  75                  80

Glu Ala Val Asn Ile Thr Asp Leu Ser Glu Asn Arg Lys Gln Asp Lys
                 85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
            115                 120                 125

Gln Pro Val Ser Leu Thr Asn Met Pro Asp Glu Gly Val Met Val Thr
130                 135                 140

Lys Phe Tyr Phe Gln Glu Asp Glu Arg Lys Cys Cys Val Glu Cys
145                 150                 155                 160

Pro Pro Cys Pro Ala Pro Pro Val Ala Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Gln Phe
            195                 200                 205

Asn Trp Tyr Val Asp Gly Val Glu Val His Asn Ala Lys Thr Lys Pro
            210                 215                 220

Arg Glu Glu Gln Phe Asn Ser Thr Phe Arg Val Val Ser Val Leu Thr
225                 230                 235                 240

Val Val His Gln Asp Trp Leu Asn Gly Lys Glu Tyr Lys Cys Lys Val
                245                 250                 255

Ser Asn Lys Gly Leu Pro Ala Pro Ile Glu Lys Thr Ile Ser Lys Thr
            260                 265                 270

Lys Gly Gln Pro Arg Glu Pro Gln Val Tyr Thr Leu Pro Pro Ser Arg
            275                 280                 285

Glu Glu Met Thr Lys Asn Gln Val Ser Leu Thr Cys Leu Val Lys Gly
            290                 295                 300

Phe Tyr Pro Ser Asp Ile Ser Val Glu Trp Glu Ser Asn Gly Gln Pro
305                 310                 315                 320

Glu Asn Asn Tyr Lys Thr Thr Pro Pro Met Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 21
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Arg Pro Ser Gly Arg Lys Ser Ser Lys Met Gln Ala Phe Arg Ile Trp
 1                   5                  10                  15

```
Asp Val Asn Gln Lys Thr Phe Tyr Leu Arg Asn Asn Gln Leu Val Ala
         20                  25                  30

Gly Tyr Leu Gln Gly Pro Asn Val Asn Leu Glu Lys Ile Asp Val
         35                  40                  45

Val Pro Ile Glu Pro His Ala Leu Phe Leu Gly Ile His Gly Gly Lys
 50                  55                  60

Met Cys Leu Ser Cys Val Lys Ser Gly Asp Glu Thr Arg Leu Gln Leu
 65                  70                  75                  80

Glu Ala Val Asn Ile Thr Asp Leu Ser Glu Asn Arg Lys Gln Asp Lys
                 85                  90                  95

Arg Phe Ala Phe Ile Arg Ser Asp Ser Gly Pro Thr Thr Ser Phe Glu
             100                 105                 110

Ser Ala Ala Cys Pro Gly Trp Phe Leu Cys Thr Ala Met Glu Ala Asp
             115                 120                 125

Gln Pro Val Ser Leu Thr Asn Met Pro Asp Glu Gly Val Met Val Thr
 130                 135                 140

Lys Phe Tyr Phe Gln Glu Asp Glu Ser Gly Ser Gly Gly Ala Ser Ser
145                 150                 155                 160

Glu Ser Ser Ala Ser Ser Asp Gly Pro His Pro Val Ile Thr Glu Ser
                 165                 170                 175

Arg Ala Ser Ser Glu Ser Ser Ala Ser Ser Asp Gly Pro His Pro Val
             180                 185                 190

Ile Thr Glu Ser Arg Glu Arg Lys Cys Cys Val Glu Cys Pro Pro Cys
             195                 200                 205

Pro Ala Pro Pro Val Ala Gly Pro Ser Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Gln Phe Asn Trp Tyr
                 245                 250                 255

Val Asp Gly Val Glu Val His Asn Ala Lys Thr Lys Pro Arg Glu Glu
             260                 265                 270

Gln Phe Asn Ser Thr Phe Arg Val Val Ser Val Leu Thr Val Val His
             275                 280                 285

Gln Asp Trp Leu Asn Gly Lys Glu Tyr Lys Cys Lys Val Ser Asn Lys
290                 295                 300

Gly Leu Pro Ala Pro Ile Glu Lys Thr Ile Ser Lys Thr Lys Gly Gln
305                 310                 315                 320

Pro Arg Glu Pro Gln Val Tyr Thr Leu Pro Pro Ser Arg Glu Glu Met
                 325                 330                 335

Thr Lys Asn Gln Val Ser Leu Thr Cys Leu Val Lys Gly Phe Tyr Pro
             340                 345                 350

Ser Asp Ile Ser Val Glu Trp Glu Ser Asn Gly Gln Pro Glu Asn Asn
             355                 360                 365

Tyr Lys Thr Thr Pro Pro Met Leu Asp Ser Asp Gly Ser Phe Phe Leu
370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                 405                 410                 415

Lys Ser Leu Ser Leu Ser Pro Gly Lys
             420                 425
```

-continued

```
<210> SEQ ID NO 22
<211> LENGTH: 19
<212> TYPE: PRT
<213> ORGANISM: Homo sapiens
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(18)
<223> OTHER INFORMATION: Any amino acid

<400> SEQUENCE: 22

Glu Glu Ser Xaa Xaa Xaa His Xaa Xaa Pro Xaa Xaa Thr Xaa Thr Xaa
1               5                   10                  15

Xaa Xaa Pro

<210> SEQ ID NO 23
<211> LENGTH: 10
<212> TYPE: PRT
<213> ORGANISM: Homo sapiens

<400> SEQUENCE: 23

Gly Val Thr Gly Thr Thr Gly Pro Ser Ala
1               5                   10
```

FUSION POLYPEPTIDES COMPRISING MUCIN-DOMAIN POLYPEPTIDE LINKERS

RELATED APPLICATIONS

This application is a divisional of U.S. application Ser. No. 13/911,834, filed Jun. 6, 2013 which claims the benefit of U.S. Provisional Application Nos. 61/657,285, filed Jun. 8, 2012; 61/778,812, filed Mar. 13, 2013; 61/657,264, filed on Jun. 8, 2012; 61/778,575, filed Mar. 13, 2013; 61/657,378, filed Jun. 8, 2012 and 61/723,081, filed Nov. 6, 2012. The entire teachings of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on May 31, 2013, is named 4000.3060WO_SL.txt and is 38,144 bytes in size.

BACKGROUND OF THE INVENTION

The construction of a fusion protein involves the linking of two proteins or domains of proteins by a peptide linker. Selection of an appropriate linker sequence is important, as it can affect the function and physical properties of the resulting fusion protein. Often flexible and hydrophilic linkers are chosen so as to not overly constrain and thereby disturb the functions of the domains. The linkers can be used to control the distance and the orientation of the domains. Fusion of a bioactive protein or peptide often results in loss of bioactivity, likely due to steric interference of the fusion partner. Additionally, in the case of Fc fusions, due to their dimeric nature, interference can also occur between the two copies of the heterologous protein.

Mucin proteins and mucin-domains of proteins contain a high degree of glycosylation which structurally allows mucin proteins and other polypeptides comprising mucin domains to behave as stiffened random coils. The present invention is based, in part, on the discovery that this stiffened random coiled structure in combination with the hydrophilic branched hydrophilic carbohydrates that make up the heavily glycosylated mucin domains is particularly useful as a linker in a fusion protein. The rod-like nature of the mucin domains can rigidly separate the bioactive protein from the fusion partner, and thereby be less susceptible to loss in activity. In the case of Fc fusions, the rigid projection away from the Fc will result in greater separation between each copy of the protein of interest, also enabling for larger fusion proteins to be expressed as Fc fusions. Also because of the high level of glycosylation, addition of a mucin domain has the potential to modify the physicochemical properties of a protein such as charge, solubility and viscoelastic properties of concentrated solutions of the active protein.

SUMMARY OF THE INVENTION

The present invention provides fusion proteins having improved bioactivity comprising a first polypeptide fusion partner and a second polypeptide fusion partner wherein the first fusion partner is linked to the second fusion partner by a mucin-domain polypeptide linker and wherein the bioactivity of the fusion protein of the invention is improved as compared to fusion of the first polypeptide fusion partner and the second polypeptide fusion partner in the absence of the mucin-domain polypeptide linker. Mucin-domain polypeptide linkers comprise a mucin domain that is rich in potential glycosylation sites, and has a high content of serine and/or threonine and proline, which can represent greater than 40% of the amino acids within the mucin domain and further comprise at least about 60% of its mass due to the glycans. Mucin domains polypeptide linkers may comprise tandem amino acid repeat units (also referred to herein as TR) that may vary in length from about 8 amino acids to 150 amino acids per each tandem repeat unit. The number of tandem repeat units may vary between 1 and 5 in a mucin-domain polypeptide linker of the invention.

Mucin-domain polypeptide linkers are capable of rigidly separating the first and second polypeptide fusion partners thereby decreasing the possibility that one fusion partner will interfere with the biological activity of the other fusion partner. The high level of glycosylation of the mucin-polypeptide linkers provides protection of proteolysis and potentially increases the solubility of the one or both of the fusion partners. When the fusion protein is a human therapeutic, the mucin-domain linker may be derived from fully human sequences and the high level of glycosylation also reduces the risk if immunogenicity in a human. The desired degree of separation between the fusion partners may be customized to provide maximum activity of the fusion protein by varying the number of tandem repeats comprising the mucin domain polypeptide.

A mucin-domain polypeptide linker may be used alone or in combination with an additional flexible linker sequence, and may also comprise a tag for purification. The mucin-domain polypeptide linker may also impart improved properties (e.g. pharmacokinetic and/or physicochemical properties) on the fusion protein compared to the fusion protein that does not comprise a mucin-domain polypeptide linker Nucleic acids encoding the polypeptides and methods for making the polypeptides are also provided. The fusion proteins of this invention can be made by transforming host cells with nucleic acid encoding the fusion, culturing the host cell and recovering the fusion from the culture, or alternatively by generating a nucleic acid construct encoding the fusion and producing the polypeptide by cell free synthesis, which synthesis may include coupled transcription and translation reactions. Also provided are vectors and polynucleotides encoding the fusion protein.

The fusion proteins may be purified and formulated in pharmacologically acceptable vehicles for administration to a patient. In one embodiment of the invention the fusion protein comprises at least one domain of an immunoglobulin, e.g. a variable region domain; a constant region domain; a single chain Fv fragment; etc. Such fusion proteins find use as immunologically specific reagents; e.g. to increase the plasma half-life of a polypeptide of interest or to target the protein to a particular cell type.

DETAILED DESCRIPTION OF THE INVENTION

Figure 1:
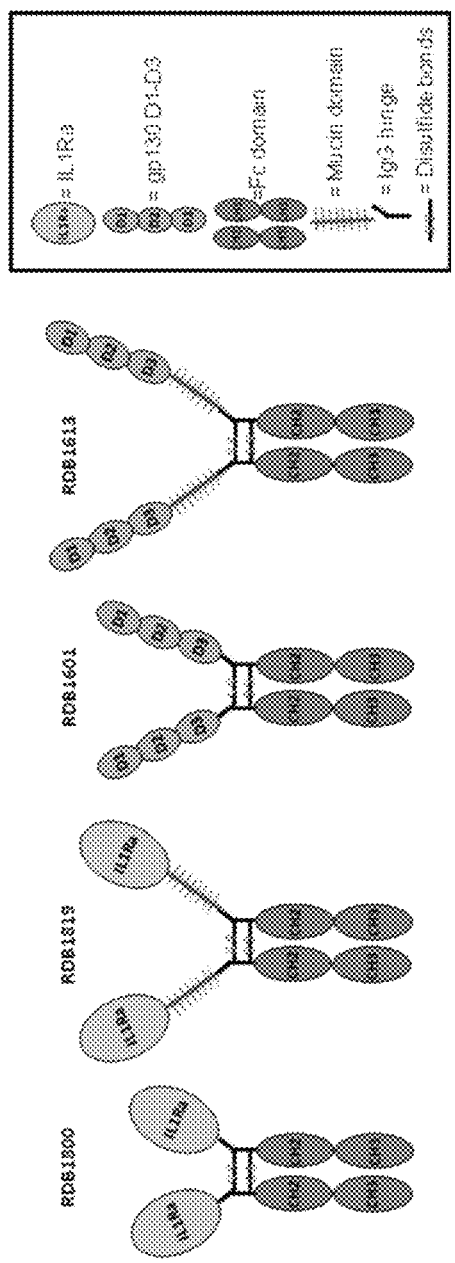
FIG. 1: Base constructs and constructs containing a mucin linker. RDB1800 is an IL-1Ra_Fc fusion protein, RDB1819 in analogous to RDB1800 but contains an intervening mucin sequence between the IL-1Ra and Fc domains. Similarly, RDB1601 is a gp130(D1-D3)Fc fusion protein, with the D1 through D3 domains of gp130 directly linked to an IgG1 Fc domain, and RDB1613 contains a mucin sequence between gp130(D1-D3) and the Fc domains.

A description of preferred embodiments of the invention follows.

Definitions

As used herein, the following terms have the meanings ascribed to them unless specified otherwise.

As used in the specification and claims, the singular forms "a", "an" and "the" include plural references unless the context clearly dictates otherwise. For example, the term "a cell" includes a plurality of cells, including mixtures thereof.

The terms "polypeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component.

As used herein the term "amino acid" refers to either natural and/or unnatural or synthetic amino acids, including but not limited to glycine and both the D or L optical isomers, and amino acid analogs and peptidomimetics. Standard single or three letter codes are used to designate amino acids.

The term "non-naturally occurring," as applied to sequences and as used herein, means polypeptide or polynucleotide sequences that do not have a counterpart to, are not complementary to, or do not have a high degree of homology with a wild-type or naturally-occurring sequence found in a mammal. For example, a non-naturally occurring polypeptide may share no more than 99%, 98%, 95%, 90%, 80%, 70%, 60%, 50% or even less amino acid sequence identity as compared to a natural sequence when suitably aligned.

The terms "glycosylation" and "glycosylated" are used interchangeably herein to mean the carbohydrate portion of a protein or the process by which sugars are post-translationally attached to proteins during their production in cells to form glyco-proteins. O-linked glycosylation of proteins is a post-translational event and refers to the attachment of glycans to serine and threonine and, to a lesser extent to hydroxyproline and hydroxylysine.

A "fragment" is a truncated form of a native active protein that retains at least a portion of the therapeutic and/or biological activity. A "variant" is a protein with sequence homology to the native active protein that retains at least a portion of the therapeutic and/or biological activity of the active protein. For example, a variant protein may share at least 70%, 75%, 80%, 85%, 90%, 95%, 96%, 97%, 98% or 99% amino acid sequence identity with the reference active protein. As used herein, the term "active protein moiety" includes proteins modified deliberately, as for example, by site directed mutagenesis, insertions, or accidentally through mutations.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is generally greater than that of its naturally occurring counterpart. In general, a polypeptide made by recombinant means and expressed in a host cell is considered to be "isolated."

An "isolated" polynucleotide or polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal or extra-chromosomal location different from that of natural cells.

"Conjugated", "linked," "fused," and "fusion" are used interchangeably herein. These terms refer to the joining together of two more chemical elements or components, by whatever means including chemical conjugation or recombinant means. For example, a promoter or enhancer is operably linked to a coding sequence if it affects the transcription of the sequence. Generally, "operably linked" means that the DNA sequences being linked are contiguous, and in reading phase or in-frame. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature).

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide that is known to comprise additional residues in one or both directions.

"Heterologous" means derived from a genotypically distinct entity from the rest of the entity to which it is being compared. For example, a glycine rich sequence removed from its native coding sequence and operatively linked to a coding sequence other than the native sequence is a heterologous glycine rich sequence. The term "heterologous" as applied to a polynucleotide, a polypeptide, means that the polynucleotide or polypeptide is derived from a genotypically distinct entity from that of the rest of the entity to which it is being compared.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a "Recombinant" as applied to a polynucleotide means that the polynucleotide is the product of various combinations of in vitro cloning, restriction and/or ligation steps, and other procedures that result in a construct that can potentially be expressed in a host cell.

The terms "gene" or "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

"Homology" or "homologous" refers to sequence similarity or interchangeability between two or more polynucleotide sequences or two or more polypeptide sequences. When using a program such as BestFit to determine sequence identity, similarity or homology between two different amino acid sequences, the default settings may be used, or an appropriate scoring matrix, such as blosum45 or blosum80, may be selected to optimize identity, similarity or homology scores. Preferably, polynucleotides that are homologous are those which hybridize under stringent conditions as defined herein and have at least 70%, preferably at least 80%, more preferably at least 90%, more preferably 95%, more preferably 97%, more preferably 98%, and even more preferably 99% sequence identity to those sequences.

The terms "stringent conditions" or "stringent hybridization conditions" includes reference to conditions under which a polynucleotide will hybridize to its target sequence, to a detectably greater degree than other sequences (e.g., at least 2-fold over background). Generally, stringency of hybridization is expressed, in part, with reference to the temperature and salt concentration under which the wash step is carried out. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short polynucleotides (e.g., 10 to 50 nucleotides) and at least about 60° C. for long polynucleotides (e.g., greater than 50 nucleotides) for example, "stringent conditions" can include hybridization in 50% formamide, 1 M NaCl, 1% SDS at 37° C., and three washes for 15 min each in 0.1×SSC/1% SDS at 60 to 65° C. Alternatively, temperatures of about 65° C., 60° C., 55° C., or 42° C. may be used. SSC concentration may be varied from about 0.1 to 2×SSC, with SDS being present at about 0.1%. Such wash temperatures are typically selected to be about 5° C. to 20° C. lower than the thermal melting point for the specific sequence at a defined ionic strength and pH. The Tm is the temperature (under defined ionic strength and pH) at which 50% of the target sequence hybridizes to a perfectly matched probe. An equation for calculating Tm and conditions for nucleic acid hybridization are well known and can be found in Sambrook, J. et al. (1989) *Molecular Cloning: A Laboratory Manual*, $2^{nd}$ ed., Vol. 1-3, Cold Spring Harbor Press, Plainview N.Y.; specifically see Volume 2 and Chapter 9. Typically, blocking reagents are used to block non-specific hybridization. Such blocking reagents include, for instance, sheared and denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be measured over the length of an entire defined polynucleotide sequence, for example, as defined by a particular SEQ ID number, or may be measured over a shorter length, for example, over the length of a fragment taken from a larger, defined polynucleotide sequence, for instance, a fragment of at least 45, at least 60, at least 90, at least 120, at least 150, at least 210 or at least 450 contiguous residues. Such lengths are exemplary only, and it is understood that any fragment length supported by the sequences shown herein, in the Tables, Figures or Sequence Listing, may be used to describe a length over which percentage identity may be measured.

"Percent (%) amino acid sequence identity," with respect to the polypeptide sequences identified herein, is defined as the percentage of amino acid residues in a query sequence that are identical with the amino acid residues of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the Tables, Figures or Sequence Listing, may be used to describe a length over which percentage identity may be measured.

A "vector" is a nucleic acid molecule, preferably self-replicating in an appropriate host, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

"Degradation resistance," as applied to a polypeptide, refers to the ability of the polypeptides to withstand degradation in blood or components thereof, which typically involves proteases in the serum or plasma, or within a formulation intended as a storage or delivery vehicle for a protein. The degradation resistance can be measured by combining the protein with human (or mouse, rat, monkey, as appropriate) blood, serum, plasma, or a formulation, typically for a range of days (e.g., 0.25, 0.5, 1, 2, 4, 8, 16 days), at specified temperatures such as −80° C., −20° C., 0° C., 4° C., 25° C., and 37° C. The intact protein in the samples is then measured using standard protein quantitation techniques. The time point where 50% of the protein is degraded is the "degradation half-life" of the protein.

The term "half-life" typically refers to the time required for the plasma concentration of a drug to be reduced by one-half. The terms "half-life", "$t_{1/2}$", "elimination half-life" and "circulating half-life" are used interchangeably herein.

"Apparent Molecular Weight" is a term referring to a measure of the relative increase or decrease in apparent molecular weight exhibited by a particular amino acid sequence. The apparent molecular weight is determined using size exclusion chromatography (SEC) and similar methods compared to globular protein standards and is measured in "apparent kD" units.

The "hydrodynamic radius" is the apparent radius ($R_h$ in nm) of a molecule in a solution calculated from diffusional properties. The "hydrodynamic radius" of a protein affects its rate of diffusion in aqueous solution as well as its ability to migrate in gels of macromolecules. The hydrodynamic radius of a protein is influenced by its molecular weight as well as by its structure, including shape and compactness, and its hydration state. Methods for determining the hydrodynamic radius are well known in the art, such as by the use of DLS and size exclusion chromatography. Most proteins have globular structure, which is the most compact three-dimensional structure a protein can have with the smallest hydrodynamic radius. Some proteins adopt a random and open, unstructured, or 'linear' conformation and as a result have a much larger hydrodynamic radius compared to typical globular proteins of similar molecular weight.

"Physiological conditions" refer to a set of conditions in a living host as well as in vitro conditions, including temperature, salt concentration, pH, that mimic those conditions of a living subject. A host of physiologically relevant conditions for use in in vitro assays have been established. Generally, a physiological buffer contains a physiological concentration of salt and is adjusted to a neutral pH ranging from about 6.5 to about 7.8, and preferably from about 7.0 to about 7.5. A variety of physiological buffers is listed in Sambrook et al. (1989). Physiologically relevant temperature ranges from about 25° C. to about 38° C., and preferably from about 35° C. to about 37° C.

"Controlled release agent", "slow release agent", "depot formulation" or "sustained release agent" are used interchangeably to refer to an agent capable of extending the duration of release of a polypeptide of the invention relative to the duration of release when the polypeptide is administered in the absence of agent.

The term "antagonist", as used herein, includes any molecule that partially or fully blocks, inhibits, or neutralizes a biological activity of a native polypeptide disclosed herein. Methods for identifying antagonists of a polypeptide may comprise contacting a native polypeptide with a candidate antagonist molecule and measuring a detectable change in one or more biological activities normally associated with the native polypeptide. In the context of the present invention, antagonists may include proteins, nucleic acids, carbohydrates, antibodies or any other molecules that decrease the effect of an active protein.

The term "agonist" is used in the broadest sense and includes any molecule that mimics a biological activity of a native polypeptide disclosed herein. Suitable agonist molecules specifically include agonist antibodies or antibody fragments, fragments or amino acid sequence variants of native polypeptides, peptides, small organic molecules, etc. Methods for identifying agonists of a native polypeptide may comprise contacting a native polypeptide with a candidate agonist molecule and measuring a detectable change in one or more biological activities normally associated with the native polypeptide.

"Activity" for the purposes herein refers to an action or effect of a component of a fusion protein consistent with that of the corresponding native active protein, wherein "biological activity" or "bioactivity" as those terms are used interchangeably herein refers to an in vitro or in vivo biological function or effect, including but not limited to receptor binding, antagonist activity, agonist activity, or a cellular or physiologic response.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect", as used herein, refers to a physiologic effect, including but not limited to the cure, mitigation, amelioration, or prevention of disease in humans or other animals, or to otherwise enhance physical or mental well-being of humans or animals, caused by a fusion protein of the invention other than the ability to induce the production of an antibody against an antigenic epitope possessed by the active protein. Determination of a therapeutically effective amount is well within the capability of those skilled in the art, especially in light of the detailed disclosure provided herein.

The terms "therapeutically effective amount" and "therapeutically effective dose", as used herein, refers to an amount of an active protein, either alone or as a part of a fusion protein composition, that is capable of having any detectable, beneficial effect on any symptom, aspect, measured parameter or characteristics of a disease state or condition when administered in one or repeated doses to a subject. Such effect need not be absolute to be beneficial.

The term "therapeutically effective dose regimen", as used herein, refers to a schedule for consecutively administered doses of an active protein, either alone or as a part of a fusion protein composition, wherein the doses are given in therapeutically effective amounts to result in sustained beneficial effect on any symptom, aspect, measured parameter or characteristics of a disease state or condition.

Fusion Proteins

In various aspects the invention provides fusion proteins comprising a first polypeptide fusion partner linked to a second polypeptide fusion partner by a mucin-domain polypeptide linker. As used herein, the terms "fusion protein" or "fusion polypeptide" or grammatical equivalents herein are meant to denote a protein composed of a plurality of protein components, which are typically unjoined in their native state but are joined by their respective amino and carboxyl termini through a mucin-domain polypeptide linker of the invention. "Protein" in this context includes proteins, polypeptides and peptides. Plurality in this context means at least two, and preferred embodiments generally utilize a first and a second polypeptide fusion partner joined through a mucin-domain polypeptide linker in accordance with the invention.

At least one or both of the first and second polypeptide fusion partners are active proteins and/or therapeutic active proteins as that term is defined herein. In one embodiment the therapeutic/biological activity of at least one of the polypeptide fusion partners is improved when linked to the other fusion partner via a mucin-domain polypeptide linker in accordance with the invention as compared to the same polypeptide fusion partners not linked via a mucin-domain polypeptide linker in accordance with the invention.

Mucin proteins and mucin-domains of proteins contain a high degree of glycosylation which structurally allows mucin proteins and other polypeptides comprising mucin domains to behave as stiffened random coils. As such, mucin domains are present in a variety of membrane-anchored adhesion molecules and receptors (including, but not limited to LDL receptor, CD164, endosialin, fractalkine, the selectins, TIM (transmembrane Ig mucin) family proteins) where their function is to extend the 'active' domain away from the cell surface for optimal interaction (Fong et al., J. Biol. Chem, 275 (6), (2000)). By analogy, the stiffened random coiled structure in combination with the hydrophilic branched hydrophilic carbohydrates that make up the heavily glycosylated mucin domains can be particularly useful for providing controlling the separation between the two fusion partners as for controlling the length and rigidity of the separation between two fusion partners.

Additionally, the hydrophilic branched hydrophilic carbohydrates that make up the heavily glycosylated mucin domains of the mucin-domain polypeptide linker are desirable for increasing the hydrodynamic radius of the fusion protein beyond what would be expected solely based on the added molecular weight. Such increase in hydrodynamic imparts desirable qualities on the fusion protein such as, for example increasing the serum half-life of a therapeutic fusion protein.

The high level of glycosylation provided by the addition of a mucin domain polypeptide linker also has the potential to modify the physicochemical properties of a protein such as charge, solubility and viscoelastic properties of concentrated solutions of the active protein.

One fusion protein design combines the binding region(s) of a first polypeptide fusion partner through a linker of the invention, to a second polypeptide fusion partner that is all or a portion of an immunoglobulin. Generally, as the term is utilized in the specification, "immunoglobulin" or "immunoglobulin domain" is intended to include all types of immunoglobulins (IgG, IgM, IgA, IgE, IgD, etc.), from all sources (e.g., human, rodent, rabbit, cow, sheep, pig, dog, other mammal, chicken, turkey, emu, other avians, etc). Immunoglobulins from humans are preferred when the fusion proteins of the invention are used for treating humans.

In one embodiment, one or more immunoglobulin fusion partners comprise the hinge and Fc regions of an immunoglobulin heavy chain. Typically, in such N-terminal fusions the encoded fusion polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the fusion proteins. In some embodiments, the fusion proteins of the invention are assembled as monomers, or hetero- or homo-multimers, and particularly as dimers or tetramers as is known in the art. Although the presence of an immunoglobulin light chain is not required, an immunoglobulin light chain might be present either covalently associated or directly fused to the polypeptide.

In one embodiment, fusion partners comprise serum albumin or a domain of serum albumin. Human serum albumin is preferred when the fusion proteins of the invention are used for treating humans. In another embodiment, fusion partners comprise human transferrin.

Of particular interest are fusion proteins for which an increase bioactivity of the fusion protein is sought as compared to the same fusion of active proteins in the absence of a mucin-domain polypeptide linker. Also of interest are fusion proteins for which an increase in a pharmacokinetic parameter such as serum half-life, increased solubility, increased stability, or some other enhanced pharmaceutical property is sought as compared to the same fusion of active proteins in the absence of a mucin-domain polypeptide linker.

The activity of the fusion protein compositions of the invention, including functional characteristics or biologic and pharmacologic activity and parameters that result, may be determined by any suitable assay known in the art for measuring the desired characteristic. The activity and structure of the fusion proteins may be measured by assays described herein, assays of the Examples, or by methods known in the art to ascertain the half-life, degree of solubility, structure and retention of biologic activity of the fusion proteins of the invention as well as comparisons with active proteins that are not fusion proteins of the invention. Quantitation of biologic activity (potency) assays include, but are not limited by, in vitro binding assays (such as ELISA, surface plasmon resonance, thermal shift assays, NMR, sedimentation, scintillation proximity, FRET, fluorescence anisotropy), in vitro cell-based assays (such as reporter-gene, phosphorylation, cell differentiation, cell growth or viability, enzyme complementarity, cell labeling), and in vivo pharmacological activities (including animal models of disease).

Fusion proteins of the invention may be produced via standard expression means without the need for further conjugation and purification steps. Mucin-domain polypeptides linkers may be linked to one or both fusion partners via either the N- or C-terminus of the fusion partner. Mucin-domain polypeptide liners are structurally less restrictive than other fusion partners in that they are monomeric, non-globular proteins having reduced bulk and a lowered risk of impact on bioactivity.

When referring to the fusion protein, the term "linked" or "fused" or "fusion" is intended to indicate that the mucin-domain polypeptide linkers and the polypeptide fusion partners are expressed as a single polypeptide in cells in a manner that allows for O-linked glycosylation of the mucin-domain polypeptide and maintains the activity of the active protein.

A fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *Current Protocols in Molecular Biology*, John Wiley & Sons, 1992). Many expression vectors are commercially available to assist with fusion moieties and will be discussed in more detail below.

Mucin-domain Polypeptide Linkers

A "mucin-domain polypeptide linker" is defined herein as any protein comprising a "mucin domain" capable of being linked to one or more fusion polypeptide partners. A mucin domain is rich in potential glycosylation sites, and has a high content of serine and/or threonine and proline, which can represent greater than 40% of the amino acids within the mucin domain. A mucin domain is heavily glycosylated with predominantly O-linked glycans. A mucin-domain polypeptide has at least about 60%, at least 70%, at least 80%, or at least 90% of its mass due to the glycans. Mucin domains may comprise tandem amino acid repeat units (also referred to herein as TR) that may vary in length from about 8 amino acids to 150 amino acids per each tandem repeat unit. The number of tandem repeat units may vary between 1 and 25 in a mucin-domain polypeptide of the invention.

Mucin-domain polypeptide linkers of the invention include, but are not limited to, all or a portion of a mucin protein. A "portion thereof" is meant that the mucin polypeptide linker comprises at least one mucin domain of a mucin protein. Mucin proteins include any protein encoded for by a MUC gene (e.g., MUC1, MUC2, MUC3A, MUC3B, MUC4, MUC5AC, MUC5B, MUC6, MUC7, MUC8, MUC9, MUC11, MUC12, MUC13, MUC15, MUC16, MUC17, MUC19, MUC20, MUC21). The mucin domain of a mucin protein is typically flanked on either side by non-repeating amino acid regions. A mucin-domain polypeptide may comprise all or a portion of a mucin protein (e.g. MUC20). A mucin-domain polypeptide may comprise all or a portion of a mucin protein of a soluble mucin protein. Preferably the mucin-domain polypeptide comprises the extracellular portion of a mucin protein.

A mucin domain polypeptide may also comprise all or a portion of a protein comprising a mucin domain but that is not encoded by a MUC gene. Such naturally occurring proteins that are not encoded by a MUC gene but that comprise mucin domains include, but are not limited to, membrane-anchored proteins such as transmembrane immunoglobulin and mucin domain (TIM) family proteins, fractalkine (neurotactin), P-selectin glycoprotein ligand 1 (PSGL-1, CD162), CD34, CD43 (leukosialin, sialophorin), CD45, CD68, CD96, CD164, GlyCAM-1, MAdCAM, E-selectin, P-selectin, L-selectin, red blood cell glycophorins, glycocalicin, glycophorin, LDL-R, ZP3, endosialin, decay accelerating factor (daf, CD55), podocalyxin, endoglycan, alpha-dystroglycan, neurofascin, EMR1, EMR2, EMR3, EMR4, ETL and epiglycanin.

A mucin-domain polypeptide linker may also comprise a non-naturally occurring polypeptide having a mucin domain as that term is defined herein. In one embodiment, the mucin-domain polypeptide is designed de novo to comprise a mucin domain in accordance with the invention.

In one embodiment, the mucin-domain polypeptide linker is not glycosylated by α1,3, galactosyltransferase or β1,6-acetylglucosaminyltransferase. In one embodiment, the fusion protein does not bind an antibody specific for an αGal. In one embodiment the fusion protein of the invention does not bind a Gal α1,3Gal specific antibody.

In one embodiment a mucin domain polypeptide linker comprises domains of tandem amino acid repeats that are rich in Pro, Ser and Thr. In one aspect of this embodiment, the number of tandem repeat units within a mucin domain polypeptide linker of the invention is between 1 and 25. Preferably, the number of tandem repeat units within a mucin domain polypeptide linker is between 2 and 20. More preferably, the number of tandem repeat units within a mucin domain polypeptide is at least about 4. In a further aspect of this embodiment, the percentage of serine and/or threonine and proline residues within a mucin domain polypeptide of the invention is at least 10%. Preferably, the percentage of serine and/or threonine and proline residues within a mucin domain polypeptide of the invention is at least 20%. More preferably, the percentage of serine and/or threonine and proline residues within a mucin domain polypeptide of the invention is greater than 30%. In a final aspect of this embodiment, each tandem amino acid repeat unit within the mucin domain is comprised of at least 8 amino acids. Preferably, each unit is comprised of at least 16 amino acids. More preferably, each unit is comprised of at least 19 amino acids, and each unit may vary in length from about 19 amino acids to 150 amino.

In one embodiment the mucin-domain polypeptide comprises at least 32 amino acids, comprising at least 40% Serine, Threonine, and Proline. In one embodiment, a mucin-domain polypeptide in accordance with the invention comprises at least 2, 4, 8, 10 or 12 tandem amino acid repeating units of at least 8 amino acids in length per tandem repeating unit. Preferred amino acid sequences of a tandem repeating unit include, but are not limited to those of Table I. The mucin-domain polypeptide, and/or nucleic acids encoding the mucin-domain polypeptide, may be constructed using mucin-domain encoding sequences of proteins that are known in the art and are publicly available through sources such as GenBank.

TABLE I

| Name | Tandem Repeat (TR) Amino Acid Sequence (# of aa's) | Number of TR/MUC* | Accession Number[+] | Notes |
|---|---|---|---|---|
| MUC1 | PAPGSTAPPAHGVTSAPDTR (20) [SEQ ID NO: 5] | 21-125; 41 and 85 are most common | P15941 | Multiple variants of MUC1 exist |
| MUC2 | ITTTTTVTPTPTPTGTQTPTTTP (23) [SEQ ID NO: 6] | 99 | Q02817 | Major TR; alternative TR sequences exist |
| MUC3 (A) | ITTTETTSHDTPSFTSS (17) [SEQ ID NO: 7] | 20 | Q02505 | Degenerate TR sequence; long serine-rich and threonine-rich sequence also exist |
| MUC4 | ATPLPVTDTSSASTGH (16) [SEQ ID NO: 8] | 145-395 | Q99102 | Degenerate TR sequence, long serine-rich and threonine-rich sequence also exist |
| MUC5AC | TTSTTSAP (8) [SEQ ID NO: 9] | (46,17,34,58)[∞] | P98088 | Consensus sequence T-T-S-T-T-S-A-P (SEQ ID NO: 9) |
| MUC5B | ATGSTATPSSTPGTTHTPPVLTTTATTPT (29) [SEQ ID NO: 10] | (11, 11, 17, 11, 23)[∞] | Q9HC84 | Degenerate TR sequence |
| MUC6 | PTS | NA | Q6W4X9 | NA |
| MUC7 | TTAAPPTPSATTQAPPSSSAPPE (23) [SEQ ID NO: 11] | 5-6 | Q8TAX7 | Degenerate TR sequence |
| MUC11/12 | EESTTVHSSPGATGTALFP (19) [SEQ ID NO: 12] | 28 | Q9UKN1 | Consensus sequence E-E-S-X-X-X-H-X-X-P-X-X-T-X-T-X-X-X-P (SEQ ID NO: 22) |
| MUC13 | PTS | NA | Q9H3R2 | |
| MUC14 | PTS | NA | | |

TABLE I-continued

| Name | Tandem Repeat (TR) Amino Acid Sequence (# of aa's) | Number of TR/MUC* | Accession Number⁺ | Notes |
|---|---|---|---|---|
| MUC15 | PTS | NA | Q8N387 | |
| MUC16 | PTS | NA | Q8WXI7 | |
| MUC17 | SSSPTPAEGTSMPTSTYSEGRTPLTSMPVSTT LVATSAISTLSTTPVDTSTPVTNSTEA (60) [SEQ ID NO: 13] | 59-60 | Q685J3 | Degenerate TR sequence |
| MUC19 | PTS | NA | Q7Z5P9 | Repeats of G-V-T-G-T-T-G-P-S-A (SEQ ID NO: 23) |
| MUC20 | SESSASSDGPHPVITPSRA (19) [SEQ ID NO: 14] | 11-12 | Q8N307 | |
| MUC21 | ATNSESSTVSSGIST (15) [SEQ ID NO: 15] | 28 | Q5SSG8 | Degenerate TR sequence |
| MUC22 | PTS | NA | E2RYF6 | |
| TIM-1 | VPTTTT (6) [SEQ ID NO: 16] | 11 | Q96D42 | Degenerate TR sequence |
| TIM-4 | PTS | NA | Q96H15 | |
| Fractalkine | Mucin-like region (PTS) | NA | P78423 | |
| Macrosialin (CD68) | Mucin-like region (PTS) | NA | P34810 | |
| CD96 | PTS | NA | P40200 | |
| Endosialin | Pro-rich region | NA | Q9HCU0 | |
| DAF (CD55) | Pro/Thr-rich region | NA | P08174 | |
| Podocalyxin | Thr-rich region | NA | O00592 | |
| EMR1 | Ser/Thr-rich region | NA | Q14246 | |
| PSGL-1 | QTTQPAATEA (10) [SEQ ID NO: 17] | 12 | Q14242 | Degenerate TR sequence |

MUC8 and MUC9 are omitted; no reliable data
PTS proline/serine/threonine rich sequence
*approximate; TR number is reported as a range in most cases
⁺Uniprot number
∞The number n of TR is different in specific regions
NA Not announced Alternatively, the mucin-domain polypeptide linker is provided as a variant mucin-domain polypeptide having a mutation in the naturally-occurring mucin-domain sequence of a wild type protein. For example, the variant mucin-domain polypeptide linker comprises additional O-linked glycosylation sites compared to the wild-type mucin-domain polypeptide. Alternatively, the variant mucin-domain polypeptide comprises amino acid sequence mutations that result in an increased number of serine, threonine or proline residues as compared to a wild type mucin-domain polypeptide Alternatively, the variant mucin-domain polypeptide sequences comprise added or subtracted charged residues, including but not limited to aspartic acid, glutamic acid, lysine, histidine, and arginine, which change the pI or charge of the molecule at a particular pH.

Active Protein and Therapeutic Active Protein

As used herein an "active protein" when referring to a polypeptide fusion partner means a protein of biologic, therapeutic, prophylactic, or diagnostic interest or function and/or is capable of mediating a biological activity. A "therapeutic active protein" as that term is used herein when referring to a polypeptide fusion partner, is a protein that is capable of preventing or ameliorating a disease, disorder or conditions when administered to a subject. In a preferred embodiment, an active protein or therapeutic active protein in accordance with the invention refers to a fusion with serum albumin (or any fragment thereof), an immunoglobulin molecule, an Fc domain of an immunoglobulin, or any fragment thereof.

An active protein of the invention can be a native, full-length protein, or can be a circularly permutated full-length protein, or can be a fragment or a sequence variant of an active protein, or can be a circularly permutated fragment or circularly permutated sequence variant of an active protein, that retains at least a portion of the therapeutic activity of the native active protein. In one embodiment, the active proteins in accordance with the invention can be a recombinant polypeptide with a sequence corresponding to a protein found in nature.

In another embodiment, the active proteins can be sequence variants, fragments, homologs, and mimetics of a natural sequence, or circularly permutated sequence variants, fragments, homologs, and mimetics of a natural sequence that retain at least a portion of the biological activity of the native active protein.

An active protein when referring to a polypeptide fusion partner of the invention can itself be a fusion polypeptide. In one embodiment, said active protein that is itself a fusion polypeptide can be a fusion polypeptide comprising two or more native, full-length proteins, or two or more circularly permutated full-length proteins, or fragments or sequence variants of two or more active proteins, or circularly permutated fragments or circularly permutated sequence variants of two or more active proteins. In a further embodiment, said active protein that is itself a fusion polypeptide can be a fusion polypeptide comprising one or more combinations of native full-length proteins, full-length circularly permutated proteins, fragments or sequence variants of active proteins, circularly permutated fragments or circularly permutated sequence variants of active proteins, that retain at least a portion of the biological activity of the native active proteins. In another embodiment, the active protein that is itself a fusion polypeptide in accordance with the invention can comprise a recombinant fusion polypeptide with sequences corresponding to proteins found in nature. In another embodiment, the active protein that is itself a fusion polypeptide can be sequence variants, fragments, homologs, and mimetics of natural sequences, or circularly permutated sequence variants, fragments, homologs, and mimetics of natural sequences that retain at least a portion of the biological activity of the native active proteins.

In non-limiting examples, the active protein can be a sequence that exhibits at least about 80% sequence identity, or alternatively 81%, 82%, 83%, 84%, 85%, 86%, 87%, 88%, 89%, 90%, 91%, 92%, 93%, 94%, 95%, 96%, 97%, 98%, 99%, or 100% sequence identity to the native active protein or a variant of a native active protein. Such proteins include but are not limited to the following: bioactive peptides (such as GLP-1, exendin-4, oxytocin, opiate peptides), cytokines, growth factors, chemokines, lymphokines, ligands, receptors, hormones, enzymes, antibodies and antibody fragments, domain antibodies, nanobodies, single chain antibodies, engineered antibody 'alternative scaffolds' such as DARPins, centyrins, adnectins, and growth factors Examples of receptors include the extracellular domain of membrane associated receptors (such as TNFRI, TNFR2, VEGF receptors, IL-1R1, IL-1RAcP, IL-4 receptor, hGH receptor, CTLA-4, PD-1, IL-6Rα, FGF receptors, cytokine receptors or accessory proteins), soluble receptors which have been cleaved from their transmembrane domains, 'dummy' or 'decoy' receptors (such as IL-1RII, TNFRSF11B, DcR3), and any chemically or genetically modified soluble receptors. Examples of enzymes include activated protein C, factor VII, collagenase; agalsidase-beta; dornase-alpha; alteplase; pegylated-asparaginase; asparaginase: and imiglucerase. Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-β), interferon gamma (IFNTγ), interferon gamma inducing factor I (IGIF), transforming growth factor beta (TGF-β). RANTES (regulated upon activation, normal T-cell expressed and presumably secreted), macrophage inflammatory proteins (e.g., MIP-1-α and MIP-1-β, *Leishmania* elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF a type 11 receptor, erythropoietin (EPO), insulin and soluble glycoproteins e.g., gp120 and gp160 glycoproteins The gp120 glycoprotein is a human immunodeficiency virus (HIV) envelope protein, and the gp160 glycoprotein is a known precursor to the gp120 glycoprotein.

In one embodiment, the biologically active polypeptide is GLP-1. In another embodiment, the biologically active polypeptide is nesiritide, human B-type natriuretic peptide (hBNP). In yet another embodiment, the biologically active polypeptide is secretin, which is a peptide hormone composed of an amino acid sequence identical to the naturally occurring porcine secretin consisting of 27 amino acids. In one embodiment, the biologically active polypeptide is enfuvirtide, a linear 36-amino acid synthetic polypeptide which is an inhibitor of the fusion of HIV-1 with CD4+ cells. In one embodiment, the biologically active polypeptide is bivalirudin, a specific and reversible direct thrombin inhibitor. Antihemophilic Factor (AHF) may be selected as the active polypeptide. In another embodiment, erythropoietin is the biologically active polypeptide. Erythropoietin is a 165 amino acid glycoprotein manufactured by recombinant DNA technology and has the same biological effects as endogenous erythropoietin. In still another embodiment, the biologically active polypeptide is Reteplase. Reteplase is a non-glycosylated deletion mutein of tissue plasminogen activator (tPA), comprising the kringle 2 and the protease domains of human tPA.

In one preferred embodiment, the active polypeptide which is Anakirna, a recombinant, nonglycosylated form of the human interleukin-1 receptor antagonist (IL-IRa). In one case, Anakinra consists of 153 amino acids and has a molecular weight of 17.3 kilodaltons. It may be produced by recombinant DNA technology using an *E. coli* bacterial expression system.

Becaplermin may also be selected as the active polypeptide. Becaplermin is a recombinant human platelet-derived growth factor (rhPDGF-BB) for topical administration. Becaplermin may be produced by recombinant DNA technology by insertion of the gene for the B chain of platelet derived growth factor (PDGF) into the yeast strain *Saccharomyces cerevisiae*. One form of Becaplermin has a molecular weight of approximately 25 kD and is a homodimer composed of two identical polypeptide chains that are bound together by disulfide bonds. The active polypeptide may be Oprelvekin, which is a recombinant form of interleukin eleven (IL-11) that is produced in *Escherichia coli* (*E. coli*) by recombinant DNA technology. In one embodiment, the selected biologically active polypeptide has a molecular mass of approximately 19,000 daltons, and is non-glycosylated. The polypeptide is 177 amino acids in length and differs from the 178 amino acid length of native IL-11 only in lacking the amino-terminal proline residue, which is known not to result in measurable differences in bioactivity either in vitro or in vivo. Yet another embodiment provides for a biologically active polypeptide which is Glucagon, a polypeptide hormone identical to human glucagon that increases blood glucose and relaxes smooth muscles of the gastrointestinal tract. Glucagon may be synthesized in a special non-pathogenic laboratory strain of E. coli bacteria that have been genetically altered by the addition of the gene for glucagon. In a specific embodiment, glucagon is a single-chain polypeptide that contains 29 amino acid residues and has a molecular weight of 3,483.

G-CSF may also be chosen as the active polypeptide Recombinant granulocyte-colony stimulating factor or G-CSF is used following various chemotherapy treatments to stimulate the recovery of white blood cells.

In one embodiment the biologically active polypeptide can be interferon alpha (IFN alpha). Chemically PEG-modified interferon-alpha 2a is clinically validated for the treatment of hepatitis C. In another embodiment the active polypeptide can be interferon gamma.

In one embodiment the biologically active polypeptide of a polypeptide fusion partner can be circularly permutated IL6. In a preferred embodiment, the biologically active polypeptide of a polypeptide fusion partner is itself a fusion polypeptide comprising circularly permutated IL-6 and the unpermutated D1 domain of gp130.

Additional cellular proteins include, but are not limited to: VEGF, VEGF-R1, VEGF-R2, VEGF-R3, Her-1, Her-2, Her-3, EGF-1, EGF-2, EGF-3, Alpha3, cMet, ICOS, CD40L, LFA-1, c-Met, ICOS, LFA-1, IL-6, B7.1, B7.2, OX40, IL-1b, TACI, IgE, BAFF, or BLys, TPO-R, CD19, CD20, CD22, CD33, CD28, IL-1-R1, TNFα, TRAIL-R1, Complement Receptor 1, FGFa, Osteopontin, Vitronectin, Ephrin A1-A5, Ephrin B1-B3, alpha-2-macroglobulin, CCL1, CCL2, CCL3, CCL4, CCL5, CCL6, CCL7, CXCL8, CXCL9, CXCL10, CXCL11, CXCL12, CCL13, CCL14, CCL15, CXCL16, CCL16, CCL17, CCL18, CCL19, CCL20, CCL21, CCL22, PDGF, TGFb, GMCSF, SCF, p40 (IL12/1L23), IL1b, IL1a, IL1ra, IL2, IL3, IL4, IL5, IL6, IL8, IL10, IL12, IL5, IL23, Fas, FasL, Fit3 ligand, 41BB, ACE, ACE-2, KGF, FGF-7, SCF, Netrin1,2, IFNa, b, g, Caspase-2, 3, 7, 8, 10, ADAM S1, S5, 8, 9, 15, TS1, TS5; Adiponectin, ALCAM, ALK-1, APRIL, Annexin V, Angiogenin, Amphiregulin, Angiopoietin-1, 2, 4, B7-1/CD80, B7-21CD86, B7-H1, B7-H2, B7-H3, Bcl-2. BACE-1, BAK, BCAM, BDNF, bNGF, bECGF, BMP2, 3, 4, 5, 6, 7, 8; CRP, Cadherin-6, 8, 11, Cathepsin A, B, C, D, E, L, S, V, X; CD11a/LFA-1, LFA-3, GP2b3a, GH receptor, RSV F protein, IL-23 (p40, p19), IL-12, CD80, CD86, CD28, CTLA-4, a4P1, a4137, TNF/Lymphotoxin, IgE, CD3, CD20, IL-6, IL-6R, BLYS/BAFF, IL-2R, HER2, EGFR, CD33, CD52, Digoxin, Rho (D), Varicella, Hepatitis, CMV, Tetanus, Vaccinia, Antivenom, Botulinum, Trail-R1, Trail-R2, cMet, TNF-R family, such as LA NGF-R, CD27, CD30, CD40, CD95, Lymphotoxin a/b receptor, Wsl-1, TL1A/TNFSF15, BAFF, BAFF-R/TNFRSF13C, TRAIL R2/TNFRSF10B, TRAIL R2/TNFRSF10B, Fas/TNFRSF6 CD27/TNFRSF7, DR3/TNFRSF25, HVEM/TNFRSF14, TROY/TNFRSF19, CD40 Ligand/TNFSF5, BCMA/TNFRSF17, CD30TNFRSF8, LIGHT/TNFSF14, 4-1 BB/TNFSF9, CD40/TNFRSF5, GITR/TNFRSF18, Osteoprotegerin/TNFRSF11B, RANK/TNFRSF11A, TRAIL R3/TNFRSF10C, TRAIL/TNFSF10, TRANCE/RANK L/TNFSF11, 4-1BB Ligand/TNFSF9, TWEAK/TNFSF12, CD40 Ligand/TNFSFS, Fas Ligand/TNFSF6, RELT/TNFRSF19L, APRIL/TNFSF13, DcR3/TNFRSF6B, TNF R1/TNFRSF1A, TRAIL R1/TNFRSF1A, TRAIL R4/TNFRSF10D, CD30 Ligand/TNFSF8, GITR Ligand/TNFSF18, TNFSF18, TACI/TNFRSF13B, NGF R/TNFRSF16, OX40 Ligand/TNFSF4, TRAIL R2/TNFRSF10B, TRAIL R3/TNFRSF10C, TWEAK R/TNFRSF12, BAFF/BLyS/TNFSF13, DR6/TNFRSF21, TNF-alpha/TNFSF1A, Pro-TNF-alpha/TNFSF1A, Lymphotoxin beta R/TNFRSF3, Lymphotoxin beta R (LTbR)/Fc Chimera, TNF R1/TNFRSF1A, TNF-beta/TNFSF1B, PGRP-S, TNF R1/TNFRSF1A, TNF RII/TNFRSF1B, EDA-A2, TNF-alpha/TNFSF1A, EDAR, XEDAR, TNF RI/TNFRSF1A 4EBP1, 14-3-3 zeta, 53BP1, 2B4/SLAMF4, CCL21/6Ckine, 4-1BB/TNFRSF9, 8D6A, 4-1BB Ligand/TNFSF9,8-oxo-dG, 4-Amino-1,8-naphthalimide, A2B5, Aminopeptidase LRAP/ERAP2, A33, Aminopeptidase N/ANPEP, Aag, Aminopeptidase P2/XPNPEP2, ABCG2, Aminopeptidase P1/XPNPEP1, ACE, Aminopeptidase PILS/ARTS1, ACE-2, Amnionless, Actin, Amphiregulin, beta-Actin. AMPK alpha 1/2, Activin A, AMPK alpha 1, Activin AB, AMPK alpha 2, Activin B, AMPK beta 1, Activin C, AMPK beta 2, Activin RIA/ALK-2, Androgen R/NR3C4, Activin RIB/ALK-4, Angiogenin, Activin RIIA, Angiopoietin-1, Activin RIIB, Angiopoietin-2, ADAMS, Angiopoietin-3, ADAM9, Angiopoietin-4, ADAM10, Angiopoietin-like 1, ADAM12, Angiopoietin-like 2, ADAM15, Angiopoietin-like 3, TACE/ADAM17, Angiopoietin-like 4, ADAM19, Angiopoietin-like 7/CDT6, ADAM33, Angiostatin, ADAMTS4, Annexin A1/Annexin I, ADAMTSS, Annexin A7, ADAMTS1, Annexin A10, ADAMTSL-1/Punctin, Annexin V, Adiponectin/Acrp30, ANP, AEBSF, AP Site, Aggrecan, APAF-1, Agrin, APC, AgRP, APE, AGTR-2, APT, AIF, APLP-1, Akt, APLP-2, Akt1, Apolipoprotein AI, Akt2, Apolipoprotein B, Akt3, APP, Serum Albumin, APRIL/TNFSF13, ALCAM, ARC, ALK-1, Artemin, ALK-7, Arylsulfatase A/ARSA. Alkaline Phosphatase, ASAH2/N-acylsphingosine Amidohydrolase-2, alpha 2u-Globulin, ASC, alpha-1-Acid Glycoprotein, ASGR1, alpha-Fetoprotein, ASK1, ALS, ATM, Ameloblastin, ATRIP, AMICA/JAML, Aurora A, AMIGO, Aurora B, AMIGO2, Axin-1, AMIGO3, Ax1, Aminoacylase/ACY1, Azurocidin/CAP37/HBP, Aminopeptidase A/ENPEP, B4GALT1, BIM, B7-1/CD80, 6-Biotin-17-NAD, B7-2/CD86, BLAME/SLAMF8, B7-H1/PD-L1, CXCL13/BLC/BCA-1, B7-H2, BLIMP1, B7-H3, Blk, B7-H4, BMI-1, BACE-1, BMP-1/PCP, BACE-2, BMP-2, Bad, BMP-3, BAFF/TNFSF13B, BMP-3b/GDF-10, BAFF R/TNFRSF13C, BMP-4, Bag-1, BMP-5, BAK, BMP-6, BAMBI/NMA, BMP-7, BARD1, BMP-8, Bax, BMP-9, BCAM, BMP-10, Bcl-10, BMP-15/GDF-9B, Bcl-2, BMPR-IA/ALK-3, Bcl-2 related protein A1, BMPR-IB/ALK-6, Bcl-w, BMPR-II, Bcl-x, BNIP3L, Bcl-xL, BOC, BCMA/TNFRSF17, BOK, BDNF, BPDE, Benzamide, Brachyury, Common beta Chain, B-Raf, beta IG-H3, CXCL14/BRAK, Betacellulin, BRCA1, beta-Defensin 2, BRCA2, BID, BTLA, Biglycan, Bub-1, Bik-like Killer Protein, c-jun, CD90/Thy1, c-Rel, CD94, CCL6/C10, CD97, Clq R1/CD93, CD151, ClqTNF1, CD160, ClqTNF4, CD163, ClqTNF5, CD164, Complement Component C1r, CD200, Complement Component C1s, CD200 R1, Complement Component C2, CD229/SLAMF3, Complement Component C3a, CD23/Fc epsilon RII, Complement Component C3d, CD2F-10/SLAMF9, Complement Component CSa, CDSL, Cadherin-4/R-Cadherin, CD69, Cadherin-6, CDC2, Cadherin-8, CDC25A, Cadherin-11, CDC25B, Cadherin-12, CDCP1, Cadherin-13, CDO, Cadherin-17, CDX4, E-Cadherin, CEACAM-1/CD66a, N-Cadherin, CEACAM-6, P-Cadherin, Cerberus 1, VE-Cadherin, CFTR, Calbindin D, cGMP, Calcineurin A, Chem R23, Calcineurin B, Chemerin, Calreticulin-2, Chemokine Sampler Packs, CaM Kinase II, Chitinase 3-like 1, cAMP, Chitotriosidase/CHIT1, Cannabinoid R1, Chk1, Cannabinoid R2/CB2/CNR2, Chk2, CAR/NR113, CHL-1/L1CAM-2, Carbonic Anhydrase I, Choline Acetyltransferase/ChAT, Carbonic Anhydrase II, Chondrolectin, Carbonic Anhydrase III, Chordin, Carbonic Anhydrase IV, Chordin-Like 1, Carbonic Anhydrase Va, Chordin-Like 2, Carbonic Anhydrase VB, CINC-1, Carbonic Anhydrase VI, CINC-2, Carbonic Anhydrase VII, CINC-3. Carbonic Anhydrase VIII, Claspin, Carbonic Anhydrase IX, Claudin-6, Carbonic Anhydrase X, CLC, Carbonic Anhydrase XII, CLEC-1, Carbonic Anhydrase XIII, CLEC-2, Carbonic Anhydrase XIV, CLECSF13/CLEC4F, Carboxymethyl Lysine, CLECSF8, Carboxypeptidase A1/CPA1, CLF-1, Carboxypeptidase A2, CL-P1/COLEC12, Carboxypeptidase A4, Clusterin, Carboxypeptidase B1, Clusterin-like 1, Carboxypeptidase E/CPE, CMG-2, Carboxypeptidase X1, CMV UL146, Cardiotrophin-1, CMV UL147. Carnosine Dipeptidase 1, CNP, Caronte, CNTF, CART, CNTF R alpha, Caspase, Coagulation Factor II/Thrombin, Caspase-1, Coagulation Factor III/Tissue Factor, Caspase-2, Coagulation Factor VII, Caspase-3, Coagulation Factor X, Caspase-4, Coagulation Factor XI, Caspase-6, Coagulation Factor XIV/Protein C, Caspase-7, COCO, Caspase-8, Cohesin, Caspase-9, Collagen I, Caspase-10, Collagen II, Caspase-12, Collagen IV, Caspase-13, Common gamma Chain/IL-2 R gamma, Caspase Peptide Inhibitors, COMP/Thrombospondin-5, Catalase, Complement Component C1rLP, beta-Catenin, Complement Component C1qA, Cathepsin 1, Complement Component C1qC, Cathepsin 3, Complement Factor D, Cathepsin 6, Complement Factor I, Cathepsin A, Complement MASP3, Cathepsin B, Connexin 43, Cathepsin C/DPPL Contactin-1, Cathepsin D, Contactin-2/TAG1, Cathepsin E, Contactin-4, Cathepsin F, Contactin-5, Cathepsin H, Corin, Cathepsin L, Comulin, Cathepsin O, CORS26/C1qTNF, 3, Cathepsin S, Rat Cortical Stem Cells, Cathepsin V, Cortisol. Cathepsin X/Z/P, COUP-TF I/NR2F1, CBP, COUP-TF II/NR2F2, CCI, COX-1, CCK-A R, COX-2, CCL28, CRACC/SLAMF7, CCR1, C-Reactive Protein, CCR2, Creatine Kinase, Muscle/CKMM, CCR3, Creatinine, CCR4, CREB, CCR5, CREG, CCR6, CRELD1, CCR7, CRELD2, CCR8, CRHBP, CCR9, CRHR-1, CCR10, CRIM1, CD155/PVR, Cripto, CD2, CRISP-2, CD3, CRISP-3, CD4, Crossveinless-2, CD4+/45RA−, CRTAM, CD4+/45RO−, CRTH-2, CD4+/CD62L−/CD44, CRY1, CD4+/CD62L+/CD44, Cryptic, CD5, CSB/ERCC6, CD6, CCL27/CTACK, CD8. CTGF/CCN², CD8+/45RA−, CTLA-4, CD8+/45RO−, Cubilin, CD9, CX3CR1, CD14, CXADR, CD27/TNFRSF7, CXCL16, CD27 Ligand/TNFSF7, CXCR3, CD28, CXCR4, CD30/TNFSF8, CXCR5, CD30 Ligand/TNFSF8, CXCR6, CD31/PECAM-1. Cyclophilin A, CD34, Cyr61/CCN1, CD36/SR-B3, Cystatin A, CD38, Cystatin B, CD40/TNFRSF5, Cystatin C, CD40 Ligand/TNFSF5, Cystatin D, CD43, Cystatin E/M, CD44, Cystatin F, CD45, Cystatin H, CD46, Cystatin-2, CD47, Cystatin S, CD48/SLAMF2, Cystatin SA, CD55/DAF, Cystatin SN, CD58/LFA-3, Cytochrome c, CD59, Apocytochrome c, CD68, Holocytochrome c, CD72, Cytokeratin 8, CD74, Cytokeratin 14, CD83, Cytokeratin 19, CD84/SLAMF5, Cytonin, D6, DISP1, DAN, Dkk-1, DANCE, Dkk-2, DARPP-32, Dkk-3, DAX1/NROB1, Dkk-4, DCC, DLEC, DCIR/CLEC4A, DLL1, DCAR, DLL4, DcR3/TNFRSF6B, d-Luciferin, DC-SIGN, DNA Ligase IV, DC-SIGNR/CD299, DNA Polymerase beta, DcTRAIL R1/TNFRSF23, DNAM-1, DcTRAIL R2/TNFRSF22, DNA-PKcs, DDR1, DNER, DDR2, Dopa Decarboxylase/DDC, DEC-205, DPCR-1, Decapentaplegic, DPP6, Decorin, DPPA4, Dectin-1/CLEC7A, DPPA5/ESG1, Dectin-2/CLEC6A, DPPII/QPP/DPP7, DEP-1/CD148, DPPIV/CD26, Desert Hedgehog, DR3/TNFRSF25, Desmin, DR6TNFRSF21, Desmoglein-1, DSCAM, Desmoglein-2, DSCAM-L1, Desmoglein-3, DSPG3, Dishevelled-1, Dtk, Dishevelled-3, Dynamin, EAR2/NR2F6, EphA5, ECE-1, EphA6, ECE-2, EphA7, ECF-L/CHI3L3, EphA8, ECM-1, EphB1, Ecotin, EphB2, EDA, EphB3, EDA-A2, EphB4, EDAR, EphB6, EDG-1, Ephrin, EDG-5, Ephrin-A1, EDG-8, Ephrin-A2, eEF-2, Ephrin-A3, EGF, Ephrin-A4, EGF R, Ephrin-A5, EGR1, Ephrin-B, EG-VEGF/PK1, Ephrin-B1, eIF2 alpha, Ephrin-B2, eIF4E, Ephrin-B3, Elk-1, Epigen, EMAP-II, Epimorphin/Syntaxin 2, EMMPRIN/CD147, Epiregulin, CXCL5/ENA, EPR-1/Xa Receptor, Endocan, ErbB2, Endoglin/CD105, ErB3, Endoglycan, ErbB4, Endonuclease III, ERCC1, Endonuclease IV, ERCC3, Endonuclease V, ERK1/ERK2, Endonuclease VIII, ERK1, Endorepellin/Perlecan, ERK2, Endostatin, ERK3, Endothelin-1, ERK5/BMK1, Engrailed-2, ERR alpha/NR3B1, EN-RAGE, ERR beta/NR3B2, Enteropeptidase/Enterokinase, ERR gamma/NR3B3, CCL11/Eotaxin, Erythropoietin, CCL24/Eotaxin-2, Erythropoietin R, CCL26/Eotaxin-3, ESAM, EpCAM/TROP-1, ER alpha/NR3A1, EPCR, ER beta/NR3A2, Eph, Exonuclease III, EphA1, Exostosin-like 2/EXTL2, EphA2, Exostosin-like 3/EXTL3, EphA3, FABP1, FGF-BP, FABP2, FGF R1-4, FABP3, FGF R1, FABP4, FGF R2, FABP5, FGF R3, FABP7, FGF R4, FABP9, FGF R5, Complement Factor B, Fgr, FADD, FHR5, FAM3A, Fibronectin, FAM3B, Ficolin-2, FAM3C, Ficolin-3, FAM3D, FITC, Fibroblast Activation Protein alpha/FAP, FKBP38, Fas/TNFRSF6, Flap, Fas Ligand/TNFSF6, FLIP, FATP1, FLRG, FATP4, FLRT1, FATP5, FLRT2, Fc gamma R1/CD64, FLRT3, Fc gamma RIIB/CD32b, Flt-3, Fc gamma RIIC/CD32c, Flt-3 Ligand, Fc gamma RIIA/CD32a, Follistatin, Fc gamma RIII/CD6, Follistatin-like 1, FcRH1/IRTA5, FosB/G0S3, FcRH2/IRTA4, FoxD3, FcRH4/IRTA1, FoxJ1, FcRH5/IRTA2, FoxP3, Fc Receptor-like 3/CD16-2, Fpg, FEN-1, FPR1, Fetuin A, FPRL1, Fetuin B, FPRL2, FGF acidic, CX3CL1/Fractalkine, FGF basic, Frizzled-1, FGF-3, Frizzled-2, FGF-4, Frizzled-3, FGF-5, Frizzled-4, FGF-6, Frizzled-5, FGF-8, Frizzled-6, FGF-9, Frizzled-7, FGF-10, Frizzled-8, FGF-11, Frizzled-9, FGF-12, Frk, FGF-13, sFRP-1, FGF-16, sFRP-2, FGF-17, sFRP-3, FGF-19, sFRP-4, FGF-20, Furin, FGF-22, FXR/NR1H4, FGF-23, Fyn, G9a/EHMT2, GFR alpha-3/GDNF R alpha-3, GABA-A-R alpha 1, GFR alpha-4/GDNF R alpha-4, GABA-A-R alpha 2, GITR/TNFRSF18, GABA-A-R alpha 4, GITR Ligand/TNFSF18, GABA-A-R alpha 5, GLI-1, GABA-A-R alpha 6, GLI-2, GABA-A-R beta 1, GLP/EHMT1, GABA-A-R beta 2, GLP-1 R, GABA-A-R beta 3, Glucagon, GABA-A-R gamma 2, Glucosamine (N-acetyl)-6-Sulfatase/GNS, GCABA-B-R2, GluR1, GAD1/GAD67, GluR2/3, GAD2/GAD65, GluR2, GADD45 alpha, GluR3, GADD45 beta, Glut1, GADD45 gamma, Glut2, Galectin-1, Glut3, Galectin-2, Glut4, Galectin-3, GlutS, Galectin-3 BP, Glutaredoxin 1, Galectin-4, Glycine R, Galectin-7, Glycophorin A, Galectin-8, Glypican 2, Galectin-9, Glypican 3, GalNAc4S-65T, Glypican 5, GAP-43, Glypican 6, GAPDH, GM-CSF, Gas1, GM-CSF R alpha, Gas6, GMF-beta, GASP-1/WFIKKNRP, gp130, GASP-2/WFIKKN, Glycogen Phosphorylase BB/GPBB, GATA-1, GPR15, GATA-2, GPR39, GATA-3, GPVI, GATA-4, GR/N1R3C1, GATA-5, Gr-1/Ly-6G, GATA-6, Granulysin, GBL, Granzyme A, GCNFNR6A1, Granzyme B, CXCL6/GCP-2, Granzyme D, G-CSF, Granzyme G, G-CSF R, Granzyme H, GDF-1, GRASP, GDF-3 GRB2, GDF-5, Gremlin, GDF-6, GRO, GDF-7, CXCL1/GRO alpha, GDF-8, CXCL2/GRO beta, GDF-9, CXCL3/GRO gamma, GDF-11, Growth Hormone, GDF-15, Growth Hormone R, GDNF, GRP75/HSPA9B, GFAP, GSK-3 alpha/beta, GFI-1, GSK-3 alpha, GFR alpha-1/GDNF R alpha-1, GSK-3 beta, GFR alpha-2/GDNF R alpha-2, EGN1T, H2AX, Histidine, H60, HFM74A, HAI-1, HMGA2, HAI-2, HMGB1, HAI-2A, TCF-2/HNF-1 beta, HAI-2B, HNF-3 beta/FoxA2, HAND1, HNF-4 alpha/NR2A1, HAPLN1, HNF-4 gamma/NR2A2, Airway Trypsin-like Protease/HAT, HO-1/HMOX1/HSP32, HB-EGF, HO-2/HMOX2, CCL14a/HCC-1, HPRG, CCL14b/HCC-3, Hrk, CCL16/HCC-4, HRP-1, alpha HCG, HS6ST2, Hck, HSD-1, HCR/CRAM-A/B, HSD-2, HDGF, HSP10/EPF, Hemoglobin, HSP27, Hepassocin, HSP60, HIES-1, HSP70, HIES-4, HSP90, HGF, HTRA/Protease Do, HGF Activator, HTRA1/PRSS11, HGF R, HTRA2/Omi, HIF-1 alpha, HVEM/TNFRSF14, HIF-2 alpha, Hyaluronan, HIN-1/Secretoglobulin 3A1,4-Hydroxynonenal, Hip, CCL1/1-309/TCA-3, IL-10, cIAP (pan), IL-10 R alpha, cIAP-1/HIAP-2, IL-10 R beta, cIAP-2/HIAP-1, IL-11, IBSP/Sialoprotein II, IL-11 R alpha, ICAM-1/CD54, 11-12, ICAM-2/CD102, IL-12/IL-23 p40, ICAM-3/CD50, IL-12 R beta 1, ICAM-5, IL-12 R beta 2, ICAT, IL-13, ICOS, IL-13 R alpha 1, Iduronate 2-Sulfatase/IDS, IL-13 R alpha 2, IFN, IL-15, IFN-alpha, IL-15 R alpha, IFN-alpha 1, IL-16, IFN-alpha 2, IL-17, IFN-alpha 4b, IL-17 R, IFN-alpha A, IL-17 RCC, IFN-alpha B2, IL-17 RD, IFN-alpha C, IL-17B, IFN-alpha D, IL-17B R, IFN-alpha F, IL-17C, IFN-alpha G, IL-17D, IFN-alpha H2, IL-17E, IFN-alpha I, IL-17F, IFN-alpha J1, IL-18/IL-1F4, IFN-alpha K, IL-18 BPa, IFN-alpha WA, IL-18 BPc, IFN-alpha/beta R1, IL-18 BPd, IFN-alpha/beta R2, IL-18 R alpha/IL-1 R5, IFN-beta, IL-18 R beta/IL-1 R7, IFN-gamma, IL-19, IFN-gamma R1, IL-20, IFN-gamma R2, 11-20 R alpha, IFN-omega, IL-20 R beta, IgE, IL-21, IGFBP-1, IL-21 R, IGFBP-2, IL-22, IGFBP-3, IL-22 R, IGFBP-4, IL-22BP, IGFBP-5, IL-23, IGFBP-6, IL-23 R, IGFBP-L1, IL-24, IGFBP-rp1/IGFBP-7, IL-26/AK155, IGFBP-rP10, IL-27, IGF-I, IL-28A, IGF-I R, IL-28B, IGF-II, IL-29/IFN-lambda 1, IGF-II R, IL-31, IgG, IL-31 RA, IgM, IL-32 alpha, IGSF2, L-33, IGSF4A/SynCAM, ILT2/CD85j, IGSF4B, ILT3/CD85k, IGSF8, ILT4/CD85d, IgY, ILT5/CD85a, IkB-beta, ILT6/CD85e, IKK alpha, Indian Hedgehog, IKK epsilon, INSRR, IKK gamma, Insulin, IL-1 alpha/IL-1F1, Insulin R/CD220, IL-1 beta/IL-1F2, Proinsulin, IL-1ra/IL-1F3, Insulysin/IDE, IL-F5/FIL1 delta, Integrin alpha 2/CD49b, IL-1F6/1FIL1 epsilon, Integrin alpha 3/CD49c, IL-1F7/FIL1 zeta, Integrin alpha 3 beta 1/VLA-3, IL-1F8/FIL1 eta, Integrin alpha 4/CD49d, IL-1F9/IL-1H1, Integrin alpha 5/CD49e, IL-1F10/IL-1HY2, Integrin alpha 5 beta 1, IL-1 R1, Integrin alpha 6/CD49f, IL-1 RII, Integrin alpha 7, IL-1 R3/IL-1 R AcP, Integrin alpha 9, IL-1 R4/ST2, Integrin alpha E/CD103, IL-1 R6/IL-1 R rp2, Integrin alpha L/CD11a, IL-1 R8, Integrin alpha L beta 2, IL-1 R9, Integrin alpha M/CD11b, IL-2, Integrin alpha M beta 2, IL-2 R alpha, Integrin alpha V/CD51, L-2 R beta, Integrin alpha V beta 5, IL-3, Integrin alpha V beta 3, IL-3 R alpha, Integrin alpha V beta 6, IL-3 R beta, Integrin alpha X/CD11c, IL-4, Integrin beta 1/CD29, IL-4 R, Integrin beta 2/CD18, IL-5, Integrin beta 3/CD61, IL-5 R alpha, Integrin beta 5, IL-6, Integrin beta 6, IL-6 R, Integrin beta 7, IL-7, CXCL10/IP-10/CRG-2, IL-7 R alpha/CD127, IRAK1, CXCR1/IL-8 RA, IRAK4, CXCR2/IL-8 RB, IRS-1, CXCL8/IL-8, Islet-1, IL-9, CXCL11/1-TAC, IL-9 R, Jagged 1, JAM-4/IGSFS, Jagged 2, JNK, JAM-A, JNK1/JNK2, JAM-B/VE-JAM, JNK1, JAM-C, JNK2, Kininogen, Kallikrein 3/PSA, Kininostatin, Kallikrein 4, KIR/CD158, Kallikrein 5, KIR2DL1, Kallikrein 6/Neurosin, KIR2DL3, Kallikrein 7, KIR2DL4/CD158d, Kallikrein 8/Neuropsin, KIR2DS4, Kallikrein 9, KIR3DL1, Plasma Kallikrein/KLKB1, KIR3DL2, Kallikrein 10, Kirrel2, Kallikrein 11, KLF4, Kallikrein 12, KLFS, Kallikrein 13, KLF6, Kallikrein 14, Klotho, Kallikrein 15, Klotho beta, KC, KOR, Keap1, Kremen-1, Kell, Kremen-2, KGF/FGF-7, LAG-3, LINGO-2, LAIR1, Lipin 2, LAIR2, Lipocalin-1, Laminin alpha 4, Lipocalin-2/NGAL, Laminin gamma 1,5-Lipoxygenase, Laminin I, LXR alpha/NR1H3, Laminin S, LXR beta/NR1H-12, Laminin-1, Livin, Laminin-5, LIX, LAMP, LMIR1/CD300A, Langerin, LMIR2CD300c, LAR, LMIR3/CD300LF, Latexin, LMIRS/CD300LB, Layilin, LMIR6/CD300LE, LBP, LMO2, LDL R, LOX-1/SR-E1, LECT2, LRH-1/NR5A2, LEDGF, LRIG1, Lefty, LRIG3, Lefty-1, LRP-1, Lefty-A, LRP-6, Legumain, LSECtin/CLEC4G, Leptin, Lumican, Leptin R, CXCL15/Lungkine, Leukotriene B4, XCL1/Lymphotactin, Leukotriene B4 R1, Lymphotoxin, LIF, Lymphotoxin beta/TNFSF3, LIF R alpha, Lymphotoxin beta R/TNFRSF3, LIGHT/TNFSF14, Lyn, Limitin, Lyp, LIMPII/SR-B2, Lysyl Oxidase Homolog 2, LIN-28, LYVE-1, LINGO-1, alpha 2-Macroglobulin, CXCL9/MIG, MAD2L1, Mimecan, MAdCAM-1, Mindin, MafB, Mineralocorticoid R/NR3C2, MafF, CCL3L1/MIP-1 alpha Isoform LD78 beta, MafG, CCL3/MIP-1 alpha, MafK, CCL4L1/LAG-1, MAG/Siglec-4-a, CCL4/MIP-1 beta, MANF, CCL15/MIP-1 delta, MAP2, CCL9/10/MIP-1 gamma, MAPK, MIP-2, Marapsin/Pancreasin, CCL19/MIP-3 beta, MARCKS, CCL20/MIP-3 alpha, MARCO, MIP-1, Mash1, MIP-II, Matrilin-2, MIP-III, Matrilin-3, MIS/AMH, Matrilin-4, MIS R11, Matriptase/ST14, MIXL1, MBL, MKK3/MKK6, MBL-2, MKK3, Melanocortin 3R/MC3R, MKK4, MCAM/CD146, MKK6, MCK-2, MKK7, Mcl-1, MKP-3, MCP-6, MLH-1, CCL2/MCP-1, MLK4 alpha, MCP-1, MMP, CCL8/MCP-2, MMP-1, CCL7/MCP-3/MARC, MMP-2, CCL13/MCP-4, MMP-3, CCL12/MCP-5, MMP-7, M-CSF, MMP-8, M-CSF R, MMP-9, MCV-type II, MMP-10, MD-1, NMP-11, MD-2, MMP-11, MMP-12, CCL22/MDC, MMP-13, MDL-1/CLECSA, MMP-14, MDM2, MMP-15, MEA-1, MMP-16/MT3-MMP, MEK1/MEK2, MMP-24/MT5-MMP, MEK1, MMP-25/MT6-MMP, MEK2, MMP-26, Melusin, MMR, MEPE, MOG, Meprin alpha, CCL23/MPIF-1, Meprin beta, M-Ras/R-Ras3, Mer, Mrell, Mesothelin, MRP1 Meteorin, MSK1/MSK2, Methionine Aminopeptidase 1, MSK1, Methionine Aminopeptidase, MSK2, Methionine Aminopeptidase 2, MSP, MFG-E8, MSP R/Ron, MFRP, Mug, MgcRacGAP, MULT-1, MGL2, Musashi-1, MGMT, Musashi-2, MIA, MuSK, MICA, MutY DNA Glycosylase, MICB, MyD88, MICL/CLEC12A, Myeloperoxidase, beta 2 Microglobulin, Myocardin, Midkine, Myocilin, MIF, Myoglobin, NAIP NGFI-B gamma/NR4A3, Nanog, NgR2/NgRH1, CXCL7/NAP-2, NgR3/NgRH2, Nbs1, Nidogen-1/Entactin, NCAM-1/CD56, Nidogen-2, NCAM-L1, Nitric Oxide, Nectin-1, Nitrotyrosine, Nectin-2/CD112, NKG2A, Nectin-3, NKG2C, Nectin-4, NKG2D, Neogenin, NKp30, Neprilysin/CD10, NKp44, Neprilysin-2/MMEL1/MMEL2, NKp46/NCR1, Nestin, NKp80/KLRF1, NETO2, NKX2.5, Netrin-1, NMDA R, NR1 Subunit, Netrin-2, NMDA R, NR2A Subunit, Netrin-4, NMDA R, NR2B Subunit, Netrin-Gla, NMDA R, NR2C Subunit, Netrin-G2a, N-Me-6,7-diOH-TIQ, Neuregulin-1/NRG1, Nodal, Neuregulin-3/NRG3, Noggin, Neuritin, Nogo Receptor, NeuroD1, Nogo-A, Neurofascin, NOMO, Neurogenin-1, Nope, Neurogenin-2, Norrin, Neurogenin-3, eNOS, Neurolysin, iNOS, Neurophysin II, nNOS, Neuropilin-1, Notch-1, Neuropilin-2, Notch-2, Neuropoietin, Notch-3, Neurotrimin, Notch-4, Neurturin, NOV/CCN3, NFAM1, NRAGE, NF-H, NrCAM, NFkB1, NRL, NFkB2, NT-3, NF-L, NT-4, NF-M, NTB-A/SLAMF6, NG2/MCSP, NTH1, NGF R/TNFRSF16, Nucleostemin, beta-NGF, Nurr-1/NR4A2, NGFI-B alpha/NR4A1, OAS2, Orexin B, OBCAM, OSCAR, OCAM, OSF-2/Periostin, OCIL/CLEC2d, Oncostatin M/OSM, OCILRP2/CLEC21, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF11B, Oligodendrocyte Marker 01, Otx2, Oligodendrocyte Marker 04, OV-6, OMgp, OX40, TNFRSF4, Opticin, OX40 Ligand/TNFSF4, Orexin A, OAS2, Orexin B, OBCAM, OSCAR, OCAM, OSF-2/Periostin, OCIL/CLEC2d, Oncostatin M/OSM, OCILRP2/CLEC21, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF11B, Oligodendrocyte Marker 01, Otx2, Oligodendrocyte Marker 04, OV-6, OMgp, OX40/TNFRSF4, Opticin, OX40 Ligand/TNFSF4, Orexin A, RACK1, Ret, Rad1, REV-ERB alphaNR1D1, Rad17, REV-ERB beta/NR1D2, Rad51, Rex-1, Rae-1, RGM-A, Rae-1 alpha, RGM-B, Rae-1 beta, RGM-C, Rae-1 delta, Rheb, Rae-1 epsilon, Ribosomal Protein S6, Rae-1 gamma, RIP1, Raf-1, ROBO1, RAGE, ROBO2, Ra1A/Ra1B, ROBO3, Ra1A, ROBO4, Ra1B, ROR/NR1F1-3 (pan), RANK/TNFRSF11A, ROR alpha/NR1F1, CCL5/RANTES, ROR gamma/NR1F3, Rap1A/B, RTK-like Orphan Receptor 1 ROR1, RAR alpha/NR1B1, RTK-like Orphan Receptor 2/ROR2, RAR beta/NR1B2, RP105, RAR gamma/NR1B3, RPA2, Ras, RSK (pan), RBP4, RSK1/RSK2, RECK, RSK1, Reg 2/PAP, RSK2, Reg I, RSK3, Reg II, RSK4, Reg III, R-Spondin 1, Reg Ma, R-Spondin 2, Reg IV, R-Spondin 3, Relaxin-1, RUNX1/CBFA2, Relaxin-2, RUNX2/CBFA1, Relaxin-3, RUNX3/CBFA3, RELM alpha, RXR alpha/NR2B1, RELM beta, RXR beta/NR2B2, RELT/TNFRSF19L, RXR gamma/NR2B3, Resistin, S100A10, SLITRK5, S100A8, SLP1, S100A9, SMAC/Diablo, S100B, Smad1, STOOP, Smad2, SALL1, Smad3, delta-Sarcoglycan, Smad4, Sca-1/Ly6, Smad5, SCD-1, Smad7, SCF, Smad8, SCF R/c-kit, SMC1, SCGF, alpha-Smooth Muscle Actin, SCL/Tall, SMUG1, SCP3/SYCP3, Snail, CXCL12/SDF-1, Sodium Calcium Exchanger 1, SDNSF/MCFD2, Soggy-1, alpha-Secretase, Sonic Hedgehog, gamma-Secretase, S or CS, beta-Secretase, S or CS3, E-Selectin, Sortilin, L-Selectin, SOST, P-Selectin, SOX1, Semaphorin 3A, SOX2, Semaphorin 3C, SOX3, Semaphorin 3E, SOX7, Semaphorin 3F, SOX9, Semaphorin 6A, SOX10, Semaphorin 6B, SOX17, Semaphorin 6C, SOX21 Semaphorin 6D, SPARC, Semaphorin 7A, SPARC-like 1, Separase, SP-D, Serine/Threonine Phosphatase Substrate 1, Spinesin, Serpin A1, F-Spondin, Serpin A3, SR-AI/MSR, Serpin A4/Kallistatin, Src, Serpin A5/Protein C Inhibitor, SREC-I/SR-F1, Serpin A8/Angiotensinogen, SREC-II, Serpin B5, SSEA-1, Serpin C1/Antithrombin-III, SSEA-3, Serpin D1/Heparin Cofactor II, SSEA-4, Serpin E1/PAI-1, ST7/LRP12, Serpin E2, Stabilin-1, Serpin F1, Stabilin-2, Serpin F2, Stanniocalcin 1, Serpin G/C1 Inhibitor, Stanniocalcin 2, Serpin 12, STAT1, Serum Amyloid A1, STAT2, SF-1/NR5A, STAT3, SGK, STAT4, SHBG, STATSa/b, SHIP, STAT5a, SHP/NROB2, STAT5b, SHP-1, STAT6, SHP-2, VE-Statin, SIGIRR, Stella/Dppa3, Siglec-2/CD22, STRO-1, Siglec-3/CD33, Substance P, Siglec-5, Sulfamidase/SGSH, Siglec-6, Sulfatase Modifying Factor 1/SUMF1, Siglec-7, Sulfatase Modifying Factor 2/SUMF2, Siglec-9, SUMO1, Siglec-10, SUMO2/3/4, Siglec-11, SUMO3, Siglec-F, Superoxide Dismutase, SIGNR1/CD209, Superoxide Dismutase-1/Cu—Zn SOD, SIGNR4, Superoxide Dismutase-2/Mn-SOD, SIRP beta 1, Superoxide Dismutase-3/EC-SOD, SKI, Survivin, SLAM/CD150, Synapsin I, Sleeping Beauty Transposase, Syndecan-1/CD138, Slit3, Syndecan-2, SLITRK1, Syndecan-3, SLITRK2, Syndecan-4, SLITRK4, TACI/TNFRSF13B, TMEFF1/Tomoregulin-1, TAO2, TMEFF2, TAPP1, TNF-alpha/TNFSF1A, CCL17/TARC, TNF-beta/TNFSF1B, Tau, TNF R1/TNFRSF1A, TC21/R-Ras2, TNF R11/TNFRSF1B, TCAM-1, TOR, TCCR/WSX-1, TP-1, TC-PTP, TP63/TP73L, TDG, TR, CCL25/TECK, TR alpha/NR1A1, Tenascin C, TR beta 1/NR1A2, Tenascin R, TR2/NR2C1, TER-119, TR4/NR2C2, TERT, TRA-1-85, Testican 1/SPOCK1, TRADD, Testican 2/SPOCK2, TRAF-1, Testican 3/SPOCK3, TRAF-2, TFPI, TRAF-3, TFPI-2, TRAF-4, TG F-alpha, TRAF-6, TGF-beta, TR AIL/TNFSF10, TGF-beta 1, TRAIL R1/TNFRSF10A, LAP (TGF-beta 1), TRAIL R2/TNFRSF10B, Latent TGF-beta 1, TRAIL R3/TNFRSF10C, TGF-beta 1.2, TRAIL R4/TNFRSF10D, TGF-beta 2, TRANCE/TNFSF11, TGF-beta 3, TfR (Transferrin R), TGF-beta 5, Apo-Transferrin, Latent TGF-beta bp1, Holo-Transferrin, Latent TGF-beta bp2, Trappin-2/Elafin, Latent TGF-beta bp4, TREM-1, TGF-beta RI/ALK-5, TREM-2, TGF-beta RII, TREM-3, TGF-beta RIIb, TREML1/TLT-1, TGF-beta RIII, TRF-1, Thermolysin, TRF-2, Thioredoxin-1, TRH-degrading Ectoenzyme/TRHDE, Thioredoxin-2, TRIMS, Thioredoxin-80, Tripeptidyl-Peptidase I, Thioredoxin-like 5/TRP14, TrkA, THOP1, TrkB, Thrombomodulin/CD141, TrkC, Thrombopoietin, TROP-2, Thrombopoietin R, Troponin I Peptide 3, Thrombospondin-1, Troponin T, Thrombospondin-2, TROY/TNFRSF19, Thrombospondin-4, Trypsin 1, Thymopoietin, Trypsin 2/PRSS2, Thymus Chemokine-1, Trypsin 3/PRSS3, Tie-1, Tryptase-5/Prss32, Tie-2, Tryptase alpha/TPS1, TIM-1/KIM-1/HAVCR, Tryptase beta-1/MCPT-7, TLM-2, Tryptase beta-2/TPSB2, TIM-3, Tryptase epsilon/BSSP-4, TIM-4, Tryptase gamma-1/TPSG1, TIM-5, Tryptophan Hydroxylase, TIM-6, TSC22, TIMP-1, TSG, TIMP-2, TSG-6, TIMP-3, TSK, TIMP-4, TSLP, TL1A/TNFSF15, TSLP R, TLR1, TSP50, TLR2, beta-III Tubulin, TLR3, TWEAK/TNFSF12, TLR4, TWEAK R/TNFRSF12, TLRS, Tyk2, TLR6, Phospho-Tyrosine, TLR9, Tyrosine Hydroxylase, TLX/NR2E1, Tyrosine Phosphatase Substrate I, Ubiquitin, UNC5H3, Ugi, UNC5H4, UGRP1, UNG, ULBP-1, uPA, iULBP-2, uPAR, ULBP-3, URB, UNC5H1, UVDE, UNC5H2, Vanilloid R1, VEGF R, VASA, VEGF R1/Flt-1, Vasohibin, VEGF R2/KDR/Flk-1, Vasorin, VEGF R3/Flt-4, Vasostatin, Versican, Vav-1, VGSQ, VCAM-1, VI-HR, VDR/NR111, Vimentin, VEGF, Vitronectin, VEGF-B, VLDLR, VEGF-C, vWF-A2, VEGF-D, Synuclein-alpha, Ku70, WASP, Wnt-7b, WIF-1, Wnt-8a WISP-1/CCN4, Wnt-8b, WNK1, Wnt-9a, Wnt-1, Wnt-9b, Wnt-3a, Wnt-10a, Wnt-4, Wnt-10b, Wnt-5a, Wnt-11, Wnt-5b, wnvNS3, Wnt7a, XCR1, XPE/DDB1, XEDAR, XPE/DDB2, Xg, XPF, XIAP, XPG, XPA, XPV, XPD, XRCC1, Yes, YY1, EphA4.

Other active polypeptides include: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleukin, denileukin diftitox, interferon alfa-n3 (injection), interferon alfa-n1, DL-8234, interferon, Suntory (gamma-1 a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP-401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphanate, octocog alfa, Factor VIIL paliferrmin, Indikinase, tenecteplase, alteplase, pamiteplase, reteplase, nateplase, monteplase, tfollitropin alfa, rFSH, hpFSH, micatfungin, pegfilgrastim, lenograstim, nartograstim, sermorelin, glucagon, exenatide, pramlintide, imiglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enfuvirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasermin, Roferon-A, interferon-alpha 2, Alfaferone, interferon alfacon-1, interferon alpha, Avonex' recombinant human luteinizing hormone, dornase alfa, trafermin, ziconotide, taltirelin, diboterminalfa, atosiban, becaplermin, eptiibatide, Zemaira, CTC-111, Shanvac-B, HPV vaccine (quadrivalent), NOV-002, octreotide, lanreotide, ancestim, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin 111, Granditropin, Vitrase, recombinant insulin, interferon-alpha (oral lozenge), GEM-21S, vapreotide, idursulfase, omapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexiganan acetate, ADI-PEG-20, LDI-200, degarelix, cintredekin besudotox, FavId, MDX-1379, ISAtx-247, liraglutide, teriparatide (osteoporosis), tifacogin, AA-4500, T4N5 liposome lotion, catumaxomab, DWP-413, ART-123, Chrysalin, desmoteplase, amediplase, corifollitropin alpha, TH-9507, teduglutide, Diamyd, DWP-412, growth hormone (sustained release injection), recombinant G-CSF, insulin (inhaled, AIR), insulin (inhaled, Technosphere), insulin (inhaled, AERX), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpimase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-1 (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-50-4798, interleukin-4, PRX-321, Pepscan, iboctadekin, rh lactoferrin, TRU-015, IL-21, ATN-161, cilengitide, Albuferon, Biphasix, IRX-2, omega interferon, PCK-3145, CAP-232, pasireotide, huN901-DM 1, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosin beta-4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, TP-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotide acetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alkaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B 19 vaccine, influenza vaccine (recombinant neuraminidase), malaria, HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93,02, MTB72F vaccine (tuberculosis), MVA-Ag85A vaccine (tuberculosis), FAR-404, BA-210, recombinant plague F1V vaccine, AG-702, OXSO-Drol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, PIA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3881L-3, TST-10088, PRO-1762, Combotox, cholecystokinin-B/gastrin-receptor binding peptides, 111In-hEGF, AE-37, trastuzumab-DM 1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A2 (injectable), ACP-HIP, SUN-11031, peptide YY [3-36](obesity, intranasal), FGLL, atacicept, BR3-Fc, BN-003, BA-058, human parathyroid hormone 1-34 (nasal, osteoporosis), F-18-CCR1, AT-1001 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TI-1-0318, BAY-73-7977, teverelix (immediate release), EP-51216, hGH (controlled release, Biosphere), OGP-I, sifuvirtide, TV-4710, ALG-889, Org-41259, rhCC10, F-991, thymopentin (pulmonary diseases), r(m) CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS 1, AC-162352, PRX-302, LFn-p24 fusion vaccine (Therapore), EP-1043, S. peumonmae pediatric vaccine, malaria vaccine, Neisserur meningutidis Group B vaccine, neonatal group B streptococcal vaccine, anthrax vaccine, HCV vaccine (gpE1+gpE2+MF-59), otitis media therapy, HCV vaccine (core antigen+ISCOMA-TRIX), hPTH(1-34) (transdermal, ViaDerm), 768974, SYN-101, PGN-0052, aviscumine, BIM-23190, tuberculosis vaccine, multi-epitope tyrosinase peptide, cancer vaccine, enkastim, APC-8024, G1-5005, ACC-001, TTS-CD3, vascular-targeted TNF (solid tumors), desmopressin (buccal controlled-release), onercept, TP-9201.

Of particular interest are known fusion proteins (linked to Fc domains, albumin, or transferrin, including bioactive peptides) comprising a therapeutic active protein that may be improved by adding (or replacing the existing linker with) a mucin-domain polypeptide linker in accordance to the invention including but not limited to, fusion proteins of: sTNFR2, CTLA4, TACI, LFA, IL-R, II-1RAcP, VEGF receptor, TPO receptor agonists, EPO receptor agonists, GLP-1, exendin-4.

The nucleic acid and amino acid sequences of numerous active proteins are well known in the art and descriptions and sequences are available in public databases such as Chemical Abstracts Services Databases (e.g., the CAS Registry), GenBank, GenPept, Entrez Nucleotide, Entrez Protein, The Universal Protein Resource (UniProt) and subscription provided databases such as GenSeq (e.g., Derwent). Polynucleotide sequences may be a wild type polynucleotide sequence encoding a given active protein (e.g., either full length or mature), or in some instances the sequence may be a variant of the wild type polynucleotide sequence (e.g., a polynucleotide which encodes the wild type active protein, wherein the DNA sequence of the polynucleotide has been optimized, for example, for expression in a particular species; or a polynucleotide encoding a variant of the wild type protein, such as a site directed mutant or an allelic variant. It is well within the ability of the skilled artisan to use a wild-type or consensus cDNA sequence or a codon-optimized variant of a active protein to create fusion protein constructs contemplated by the invention using methods known in the art and/or in conjunction with the guidance and methods provided herein, and described more fully in the Examples.

Pharmacokinetic Properties of the Fusion Proteins

The invention provides fusion proteins of therapeutic active proteins with enhanced pharmacokinetics compared to the therapeutic active protein not linked to a mucin-polypeptide domain, that, when used at the optimal dose determined for the composition by the methods described herein, can achieve enhanced pharmacokinetics compared to a comparable dose of the therapeutic active protein not linked to a mucin-domain polypeptide in accordance with the invention. As used herein, a "comparable dose" means a dose with an equivalent moles/kg for the therapeutic active protein that is administered to a subject in a comparable fashion. It will be understood in the art that a "comparable dosage" of the fusion protein would represent a greater weight of agent but would have essentially the same mole-equivalents of the therapeutic active protein in the dose of the fusion protein and/or would have the same approximate molar concentration relative to the therapeutic active protein.

Pharmacokinetic properties that may be enhanced by using a mucin-domain polypeptide linker in accordance with the invention include, but are not limited to half-life, Tmax, Cmax (in this case, enhancement refers to the reduction of peak-to-trough differences), distribution, or duration of action through a combination of the individual effects.

Physicochemical and Pharmaceutical Properties

In addition to enhancing the PK properties of a therapeutic, a fusion protein comprising a mucin-domain polypeptide linker may useful for improving the pharmaceutical or physicochemical properties (such as the degree of aqueous solubility) of the therapeutic active peptide or protein. Solubility improvements can be mediated both through addition of the highly hydrophilic carbohydrates on the mucin as well as through selection of the proper mucin-polypeptide sequence, which may additionally contain ionizable residues such as aspartic acid, glutamic acid, histidine, lysine, and arginine. The ionizable residues result in the modulation of the pI of the fusion protein and thereby the total charge of the protein in a formulation approaching physiological pH and tonicity.

The fusion proteins of the invention can be constructed and assayed, using methods described herein, to confirm the physicochemical properties of the fusion protein result in the desired properties. In one embodiment, the mucin-domain polypeptide is selected such that the fusion protein has an aqueous solubility that is within at least about 25% greater compared to a therapeutic active protein not linked to the fusion protein, or at least about 30%, or at least about 40%, or at least about 50%, or at least about 75%, or at least about 100%, or at least about 200%, or at least about 300%, or at least about 400%, or at least about 500%, or at least about 1000% greater than the corresponding therapeutic active protein not containing the mucin domain linker.

Uses of the Fusion Proteins

In another aspect, the invention provides a method of for achieving a beneficial effect in a disease, disorder or condition mediated by therapeutic active protein. The present invention addresses certain disadvantages and/or limitations of therapeutic active proteins when fused to a polypeptide fusion partner in the absence of a mucin-domain polypeptide linker.

In one embodiment, the invention provides a method for achieving a beneficial effect in a subject comprising the step of administering to the subject a therapeutically or prophy-lactically-effective amount of a fusion protein. The effective amount can produce a beneficial effect in helping to treat a disease or disorder. In some cases, the method for achieving a beneficial effect can include administering a therapeutically effective amount of a fusion protein composition to treat a subject for diseases and disease categories wherein a therapeutic protein or peptide does not exist.

Diseases amenable to treatment by administration of the compositions of the invention include without limitation cancer, inflammatory diseases, arthritis, osteoporosis, infections in particular hepatitis, bacterial infections, viral infections, genetic diseases, pulmonary diseases, diabetes, hormone-related disease, Alzheimer's disease, cardiac diseases, myocardial infarction, deep vain thrombosis, diseases of the circulatory system, hypotension, hypertension, allergies, pain relief, dwarfism and other growth disorders, intoxications, blot clotting diseases, diseases of the innate immune system, embolism, wound healing, healing of burns, Crohn's disease, asthma, ulcer, sepsis, glaucoma, cerebrovascular ischemia, respiratory distress syndrome, corneal ulcers, renal disease, diabetic foot ulcer, anemia, factor IX deficiency, factor VIII deficiency, factor VII deficiency, mucositis, dysphagia, thrombocyte disorder, lung embolism, infertility, hypogonadism, leucopenia, neutropenia, endometriosis, Gaucher disease, obesity, lysosome storage disease, AIDS, premenstrual syndrome, Turners syndrome, cachexia, muscular dystrophy, Huntington's disease, colitis, SARS, Kaposi sarcoma, liver tumor, breast tumor, glioma, Non-Hodgkin lymphoma, Chronic myelocytic leukemia; Hairy cell leukemia; Renal cell carcinoma; Liver tumor; Lymphoma; Melanoma, multiple sclerosis, Kaposis sarcoma, papilloma virus, emphysema, bronchitis, periodontal disease, dementia, parturition, non-small cell lung cancer, pancreas tumor, prostate tumor, acromegaly, psoriasis, ovary tumor, Fabry disease, lysosome storage disease.

In one embodiment, the method comprises administering a fusion protein in accordance with the invention comprising to a mucin-domain polypeptide linker and at least one pharmaceutically acceptable carrier to a subject in need thereof that results in greater improvement in at least one parameter, physiologic condition, or clinical outcome mediated by the fusion protein compared to the effect mediated by administration of a pharmaceutical composition comprising a fusion protein in the absence of a mucin-domain polypeptide linker administered at a comparable dose. In one embodiment, the pharmaceutical composition is administered at a therapeutically effective dose. In another embodiment, the pharmaceutical composition is administered using multiple simultaneous or sequential doses using a therapeutically effective dose regimen (as defined herein) for the length of the dosing period.

A therapeutically effective amount of a fusion protein may vary according to factors such as the disease state, age, sex, and weight of the individual, and the ability of the antibody or antibody portion to elicit a desired response in the individual. A therapeutically effective amount is also one in which any toxic or detrimental effects of the fusion protein are outweighed by the therapeutically beneficial effects. A prophylactically effective amount refers to an amount of fusion protein required for the period of time necessary to achieve the desired prophylactic result.

In another aspect, the invention provides methods of making fusion proteins to result in increased stability, increased water solubility, and/or ease of formulation, as compared to the native therapeutic active proteins. In one embodiment, the invention includes a method of increasing the aqueous solubility of a fusion protein as compared to a fusion protein that does not comprise a mucin-domain polypeptide linker. Factors that contribute to the property of mucin-domain polypeptide linker to confer increased water solubility on a fusion protein include the high percentage of glycosylation, the type of glycans, and the charge on the amino acids of the mucin-domain polypeptide. In some embodiments, the method results in a fusion protein wherein the water solubility is at least about 50%, or at least about 60% greater, or at least about 70% greater, or at least about 80% greater, or at least about 90% greater, or at least about 100% greater, or at least about 150% greater, or at least about 200% greater, or at least about 400% greater, or at least about 600% greater, or at least about 800% greater, or at least about 1000% greater, or at least about 2000% greater, or at least about 4000% greater, or at least about 6000% greater under physiologic conditions, or in a therapeutically acceptable formulation, compared to the native therapeutic active protein.

Nucleic Acid Sequences

The present invention provides isolated polynucleic acids encoding fusion proteins and sequences complementary to polynucleic acid molecules encoding fusion proteins of the invention. In another aspect, the invention encompasses methods to produce polynucleic acids encoding fusion proteins of the invention and sequences complementary to fusion proteins of the invention, including homologous variants. In general, the invention provides methods of producing a polynucleotide sequence coding for a fusion protein and expressing the resulting gene product include assembling nucleotides encoding each of the mucin-domain polypeptides and active proteins, linking the components in frame, incorporating the encoding gene into an appropriate expression vector, transforming an appropriate host cell with the expression vector, and causing the fusion protein to be expressed in the transformed host cell, thereby producing the fusion protein of the invention. Standard recombinant techniques in molecular biology can be used to make the polynucleotides and expression vectors of the present invention. In accordance with the invention, nucleic acid sequences that encode a fusion protein may be used to generate recombinant DNA molecules that direct the expression of fusion proteins in appropriate host cells. Several cloning strategies are envisioned to be suitable for performing the present invention, many of which can be used to generate a construct that comprises a gene coding for a fusion protein or its complement. In one embodiment, the cloning strategy would be used to create a gene that encodes a monomeric fusion protein that comprises an active protein and a mucin-domain polypeptide. In the foregoing embodiments hereinabove described in this paragraph, the gene can further comprise nucleotides encoding spacer sequences that may also encode cleavage sequence(s).

In one approach, a construct is first prepared containing the DNA sequence corresponding to a fusion protein. DNA encoding an active protein and/or a mucin polypeptide domain may be obtained from a cDNA library prepared using standard methods from tissue or isolated cells believed to possess the mRNA of an active protein and to express it at a detectable level. If necessary, the coding sequence can be obtained using conventional primer extension procedures as described in Sambrook, et al., supra, to detect precursors and processing intermediates of mRNA that may not have been reverse-transcribed into cDNA. Accordingly, DNA can be conveniently obtained from a cDNA library prepared from such sources. The encoding gene(s) may also be obtained from a genomic library or created by standard synthetic procedures known in the art (e.g., automated nucleic acid synthesis) using DNA sequences obtained from publicly available databases, patents, or literature references. Such procedures are well known in the art and well described in the scientific and patent literature. For example, sequences can be obtained from Chemical Abstracts Services (CAS) Registry Numbers (published by the American Chemical Society) and/or GenBank Accession Numbers available through the National Center for Biotechnology Information (NCBI) webpage, available on the world wide web at ncbi.nlm.nih.gov that correspond to entries in the CAS Registry or GenBank database that contain an amino acid sequence of the active protein or of a fragment or variant of the active protein or of the mucin-domain polypeptide.

A gene or polynucleotide encoding one or both of the polypeptide fusion partners can be then be cloned into a construct, which can be a plasmid or other vector under control of appropriate transcription and translation sequences for high level protein expression in a biological system. In a later step, a second gene or polynucleotide coding for the mucin-domain polypeptide linker, for example, is genetically fused to the nucleotides encoding the N- and/or C-terminus of the polypeptide fusion partners by cloning it into the construct adjacent and in frame nucleotides encoding the fusion partners.

The resulting polynucleotides encoding the fusion proteins can then be individually cloned into an expression vector. The nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Such techniques are well known in the art and well described in the scientific and patent literature.

Suitable vectors, hosts, and expression systems are well known to those skilled in the art of recombinant expression. Various vectors are publicly available. The vector may, for example, be in the form of a plasmid, cosmid, viral particle, or phage. Both expression and cloning vectors contain a nucleic acid sequence that enables the vector to replicate in one or more selected host cells, and further allows expression and post-translational modification of the recombinant protein within the host cell.

The present invention also provides a host cell for expressing the monomeric fusion protein compositions disclosed herein. Examples of suitable eukaryotic host cells include, but are not limited to yeast hosts such as *Saccharomyces cerevisiae, Pichia pastoris*, and *Hansenula polymorpha*; insect hosts such as *Spodoptera frupperda* Sf9, *Spodoptera frugiperda* Sf21, and High Five cells; and mammalian hosts such as mouse fibroblast cells (C 127-BPV), Chinese hamster ovary cells (CHO-DHFR, CHO-NEO-SPLA, CHO-GS), and mouse myeloma cells (NSO-GS).

Expressed fusion proteins may be purified via methods known in the art or by methods disclosed herein. Procedures such as gel filtration, affinity purification, salt fractionation, ion exchange chromatography, size exclusion chromatography, hydroxyapatite adsorption chromatography, hydrophobic interaction chromatography and gel electrophoresis may be used; each tailored to recover and purify the fusion protein produced by the respective host cells. Methods of purification are described in Robert K. Scopes, Protein Purification: Principles and Practice, Charles R. Castor (ed.), Springer-Verlag 1994, and Sambrook, et al., supra. Multi-step purification separations are also described in Baron, et al., *Crit. Rev. Biotechnol.* 10:179-90 (1990) and Below, et al., *J. Chromatogr. A.* 679:67-83 (1994).

Pharmaceutical Compositions

The present invention provides pharmaceutical compositions comprising fusion proteins of the invention. In one embodiment, the pharmaceutical composition comprises the fusion protein and at least one pharmaceutically acceptable carrier. Fusion proteins of the present invention can be formulated according to known methods to prepare pharmaceutically useful compositions, whereby the polypeptide is combined with a pharmaceutically acceptable carrier vehicle, such as aqueous solutions or buffers, pharmaceutically acceptable suspensions and emulsions. Examples of non-aqueous solvents include propyl ethylene glycol, polyethylene glycol and vegetable oils. Therapeutic formulations are prepared for storage by mixing the active ingredient having the desired degree of purity with optional physiologically acceptable carriers, excipients or stabilizers, as described in Remington's Pharmaceutical Sciences 16th edition, Osol, A. Ed. (1980), in the form of lyophilized formulations or aqueous solutions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition, the pharmaceutical compositions can also contain other pharmaceutically active compounds or a plurality of compounds of the invention.

More particularly, the present pharmaceutical compositions may be administered for therapy by any suitable route including oral, rectal, nasal, topical (including transdermal, aerosol, buccal and sublingual), vaginal, parenteral (including subcutaneous, subcutaneous or intrathecally by infusion pump, intramuscular, intravenous and intradermal), intravitreal, and pulmonary. It will also be appreciated that the preferred route will vary with the therapeutic agent, condition and age of the recipient, and the disease being treated.

In one preferred embodiment, the composition is formulated in accordance with routine procedures as a pharmaceutical composition adapted for intravenous administration to human beings. Typically, compositions for intravenous administration are solutions in sterile isotonic aqueous buffer. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In one preferred embodiment, the pharmaceutical composition is administered subcutaneously. In this embodiment, the composition may be supplied as a lyophilized powder to be reconstituted prior to administration. The composition may also be supplied in a liquid form, which can be administered directly to a patient. In one embodiment, the composition is supplied as a liquid in a pre-filled syringe such that a patient can easily self-administer the composition.

In another embodiment, the compositions of the present invention are encapsulated in liposomes, which have demonstrated utility in delivering beneficial active agents in a controlled manner over prolonged periods of time. Liposomes are closed bilayer membranes containing an entrapped aqueous volume. Liposomes may also be unilamellar vesicles possessing a single membrane bilayer or multilamellar vesicles with multiple membrane bilayers, each separated from the next by an aqueous layer. The structure of the resulting membrane bilayer is such that the hydrophobic (non-polar) tails of the lipid are oriented toward the center of the bilayer while the hydrophilic (polar) heads orient towards the aqueous phase. In one embodiment, the liposome may be coated with a flexible water soluble polymer that avoids uptake by the organs of the mononuclear phagocyte system, primarily the liver and spleen. Suitable hydrophilic polymers for surrounding the liposomes include, without limitation, PEG, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose hydroxyethylcellulose, polyethyleneglycol, polyaspartamide and hydrophilic peptide sequences as described in U.S. Pat. Nos. 6,316,024; 6,126,966; 6,056,973 and 6,043,094, the contents of which are incorporated by reference in their entirety.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phasphatidylglycerol, phosphatidylinositol, and sphingomyelin as disclosed in U.S. Pat. Nos. 6,056,973 and 5,874,104. The vesicle-forming lipids may also be glycolipids, cerebrosides, or cationic lipids, such as 1,2-dioleyloxy-3-(trimethylamino) propane (DOTAP); N-[1-(2,3,-ditetradecyloxy) propyl]-N,N-dimethyl-N-hydroxyethylammonium bromide (DMRIE); N-[1-(2,3,-dioleyloxy)propyl]-N,N-dimethyl-N-hydroxy ethyl ammonium bromide (DORIE); N-[1-(2,3-dioleyloxy)propyl]-N,N,N-trimethylammonium chloride (DOTMA); 3 [N—(N',N'-dimethylaminoethane) carbamoly] cholesterol (DC-Chol); or dimethyldioctadecylammonium (DDAB) also as disclosed in U.S. Pat. No. 6,056,973. Cholesterol may also be present in the proper range to impart stability to the vesicle as disclosed in U.S. Pat. Nos. 5,916,588 and 5,874,104.

For liquid formulations, a desired property is that the formulation be supplied in a form that can pass through a 25, 28, 30, 31, 32 gauge needle for intravenous, intramuscular, intraarticular, or subcutaneous administration.

In other embodiments, the composition may be delivered via intranasal, buccal, or sublingual routes to the brain to enable transfer of the active agents through the olfactory passages into the CNS and reducing the systemic administration. Devices commonly used for this route of administration are included in U.S. Pat. No. 6,715,485. Compositions delivered via this route may enable increased CNS dosing or reduced total body burden reducing systemic toxicity risks associated with certain drugs. Preparation of a pharmaceutical composition for delivery in a subdermally implantable device can be performed using methods known in the art, such as those described in, e.g., U.S. Pat. Nos. 3,992,518; 5,660,848; and 5,756,115.

EXAMPLES

The following examples are offered by way of illustration and are not to be construed as limiting the invention as claimed in any way.

Example 1

IL-1Ra-mucin-Fc Fusion Protein Activity In Vitro

Fusion proteins of human IL-1Ra with the Fc domain from IgG1 were made where the IL-1Ra was either directly linked through the IgG1 hinge (RDB1800) (SEQ ID NO:1) or where 2 tandem repeats from human MUC20 were inserted between the Fc domain and IL-1Ra (RDB1819) (SEQ ID NO:2). The genes were synthetically synthesized (Geneart) and cloned into pcDNA™ (Invitrogen), then transiently expressed in CHO-S cells using FreeStyle™ MAX Reagent (Life Technologies). Proteins were purified using Protein A (GE Healthcare) and dialyzed against PBS.

HEK-Blue™ IL-1β cells (InvivoGen) are human embryonic kidney cells specifically designed to detect bioactive IL-1β in vitro by monitoring the IL-1β-induced activation of the NF-κB/AP-1 pathways. The cell line expresses an inducible secreted embryonic alkaline phosphatase (SEAP) reporter gene under control of the IFN-β minimal promoter fused to five Mkt) and five AP-1 binding sites. For the IL-1β antagonist assay, HEK-Blue IL-1β cells were plated at 50,000 cells/well in DMEM media containing 2 mM L-glu and 10% heat inactivated FBS (Gibco) and 57 pM IL-1β (R&D systems). Cells were incubated for 20 hours at 37° C., 5% $CO_2$ with varying concentrations of IL-1Ra, RDB1800 or RDB1819. SEAP production was detected by adding QUANTI-Blue™ (InvivoGen) and incubating for 3 hours at 37° C., 5% $CO_2$ and then read on a plate reader at 630 nm.

Figure 2:
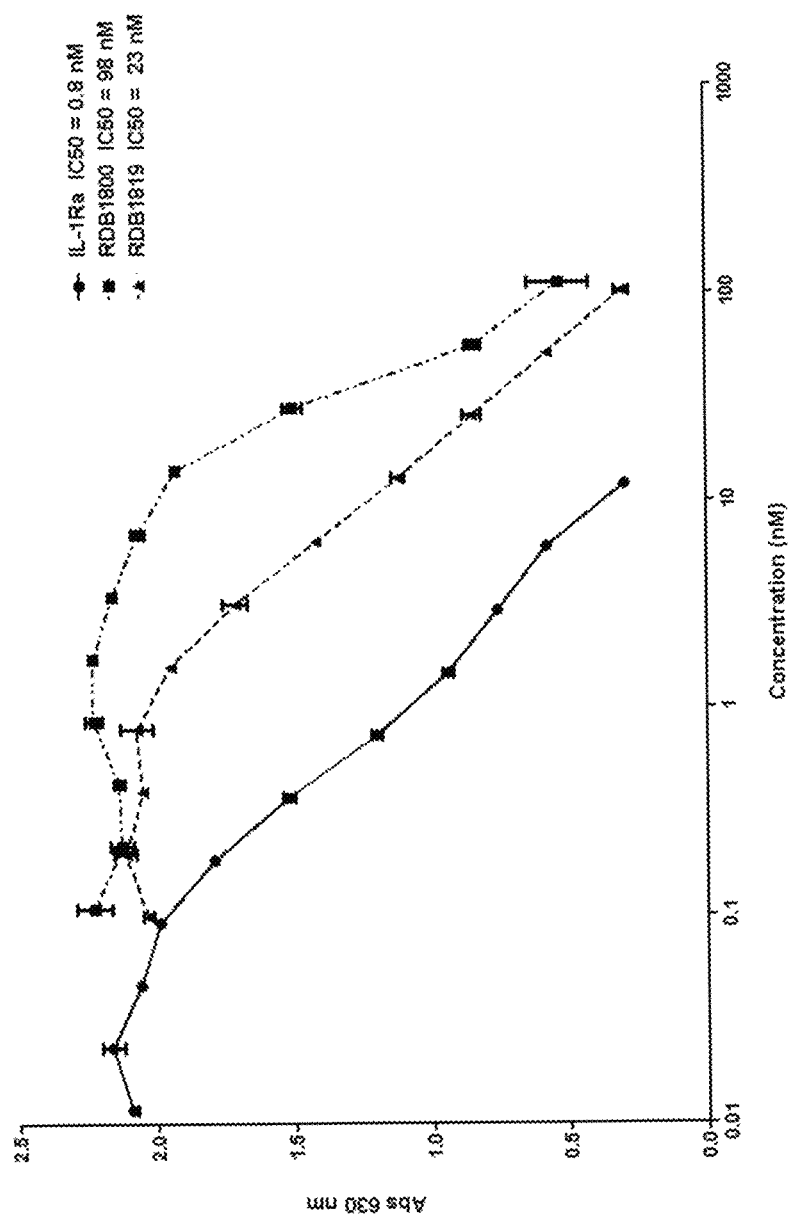
FIG. 2: Inhibition of IL1β signaling by IL-1Ra (●), RDB1800 (-■-) and RDB1819 (▲) in the HEK- Blue™ cell assay. Estimated values of $IC_{50}$ are reported in the top right corner of the figure.

IL-1β activation of the SEAP gene can be inhibited by the IL-1β antagonist IL-1Ra in a dose dependent manner. Loss of activity was observed for IL-1Ra when directly fused to Fc (RDB1800). Incorporation of the mucin domain between IL-1Ra and Fc partially restores the inhibitory activity of the IL-1Ra_Fc fusion molecule from an $IC_{50}$ of 98 nM for 1800, to 23 nM for RDB1819 (FIG. 2).

Example 2

Molecular Weight Measurement

The addition of the mucin sequence is likely leading to a large increase in 0-glycosylation, and thus a larger hydrodynamic volume. RDB1800 and RDB1819 were characterized by analytical gel filtration on a Superdex 200 10/300 GL column (GE Healthcare). The column was equilibrated at 0.5 ml/min with PBS, pH 7.4 as a running buffer for all analyses. After equilibration, protein molecular weight standards (Gel Filtration HMW calibration kit; GE Healthcare) were injected at a flow rate of 0.5 ml/min in order to determine elution volume to generate a molecular weight standard curve. Purified samples of RDB1800 and RDB1819 were then injected in separate runs at 0.5 mL/min to determine elution volume. Apparent molecular weights of RDB1800 and RDB1819 were determined by interpolation using the standard curve generated from the elution volumes of the different molecular weight standards.

Figure 3:
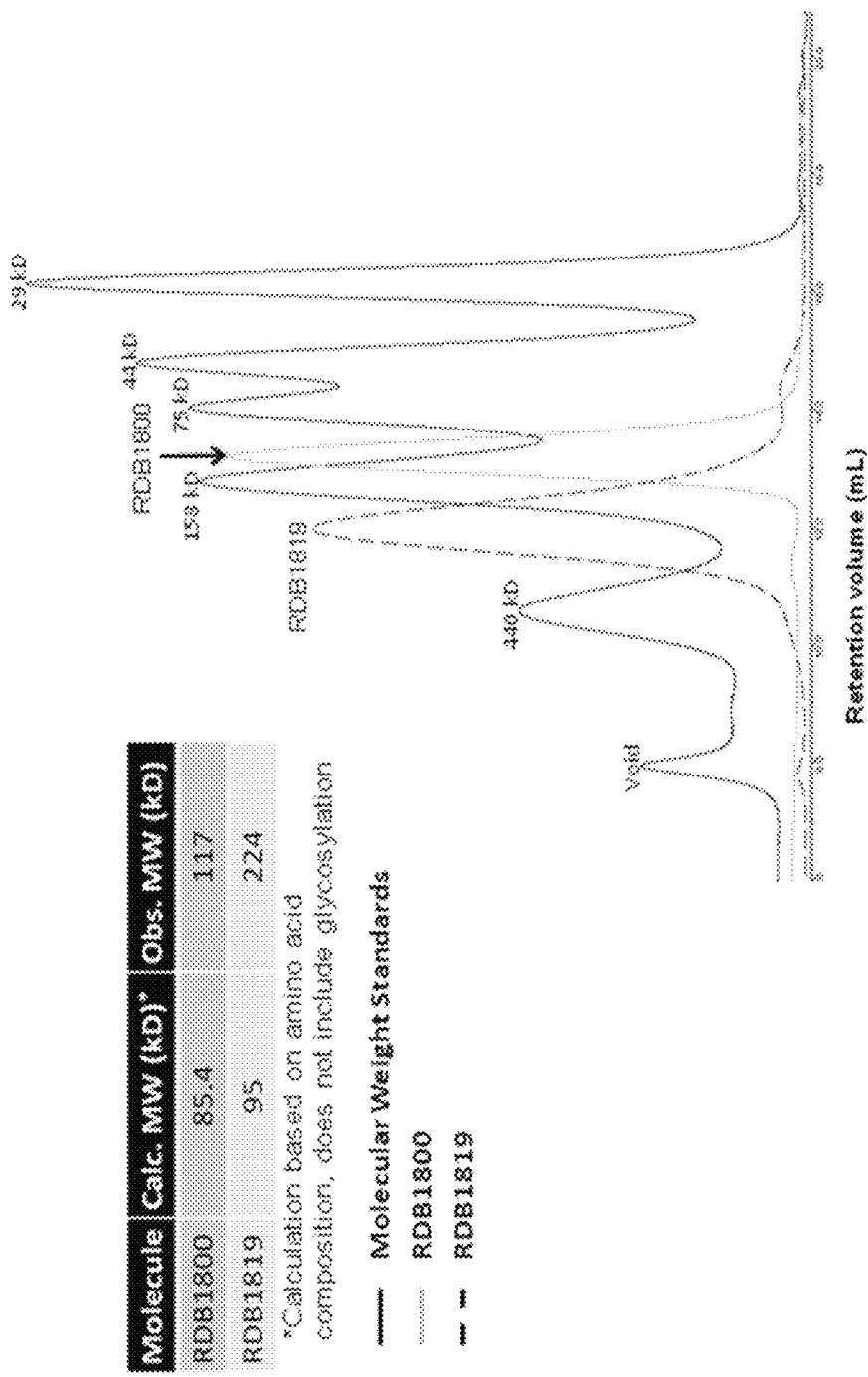
FIG. 3: Gel filtration chromatogram of RDB1800 (light grey) and RDB1819 (dashed, dark grey) and molecular size standards (solid, dark grey). Molecular weights of the standards are listed above their eluting peaks.

The apparent molecular weight of RDB1800 and RDB1819 was observed by analytical size exclusion chromatography. There are a total of 4 N-linked glycosylation sites present in RDB1800 and 1819, one in each IL-Ra arm and one in each Fc portion of the molecule. The calculated molecular weight for RDB1800 is 85.4 kDa with an observed size of 117 kDa. This observation is consistent with the presence of N-glycosylation and the flexible hinge connecting IL1Ra and Fc. The addition of the mucin linker adds multiple O-linked glycosylation sites and a more rigid rod-like hinge region resulting in an observed size of 224 kDa compared to a 95 kDa calculated molecular weight for RDB1819 (FIG. 3).

Example 3

IL-1Ra-mucin-Fc Fusion Protein Activity In Vivo

Collagen antibody-induced arthritis (CAIA) is a mouse model of rheumatoid arthritis (RA) that is known to involve the IL-1 pathway. Arthritis was stimulated on Day "−3" by administration of a cocktail of monoclonal antibodies that are directed at conserved auto-antigenic epitopes in collagen type II. At Day "0" an LPS endotoxin boost was administered, along with single subcutaneous (SC) injections of 20 mg/kg of RDB1800 or RDB1819. A group of ten mice were used for each treatment. Mouse paw volume displacement was measured across multiple days to assess the degree of paw inflammation.

Figure 4:
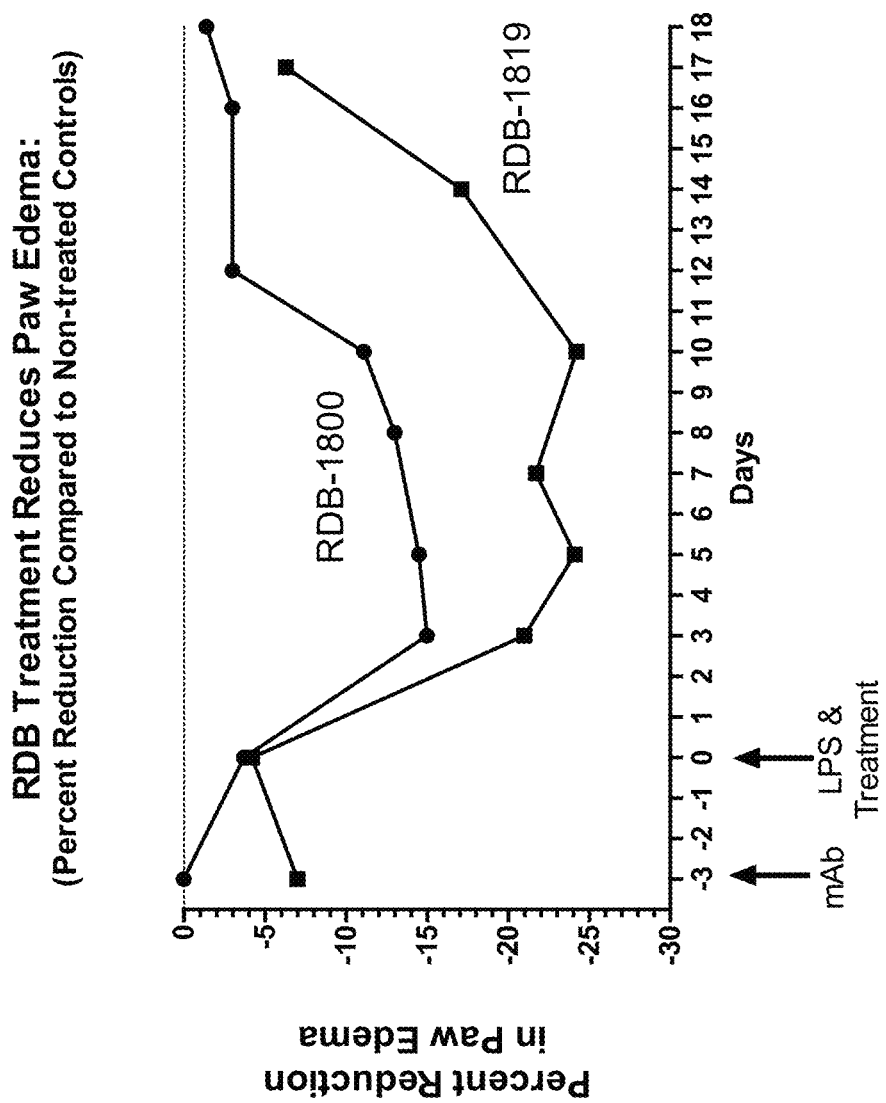
FIG. 4: The inhibitory effects of a single 20 mg/kg injection of RDB1800 and RDB1819 in the mouse CAIA model of inflammation. The black arrows indicate the days of injection with the monoclonal antibody cocktail (mAb) and with LPS and treatment molecule. The % reduction in paw edema was calculated for each compound compared to saline control. A group of ten mice were used for each treatment.

RDB1800 and RDB1819 significantly reduced paw edema for up to 10 days and 14 days after injection respectively, as compared to the Saline control group. Additionally, the increased potency observed in the in vitro HEK bioassay correlates with an increase in potency in the in vivo CAIA model with RDB1819 showing a statistically significant difference in paw reduction compared to RDB1800 (FIG. 4).

Example 4

Inhibition of IL-6-dependent Differentiation of M1 Cells by Gp130-mucin-Fc Fusion Construct Fusion proteins comprising a truncated human gp130 comprising domains D1-D3 and the Fc domain from IgG1 were made +/−mucin domains (RDB1601, SEQ ID NO:3 and RDB1613 SEQ ID NO: 4). The genes were synthetically synthesized (Geneart) and cloned into pcDNA™ (Invitrogen) and transiently expressed in CHO-S cells using FreeStyle™ MAX Reagent (Life Technologies). Proteins were purified using Protein A (GE Healthcare) and dialyzed against PBS.

In vitro bioactivity was assessed by evaluating the ability of RDB1601 and RDB1613 to inhibit IL-6-dependent differentiation of M1 cells, as measured by the percent of CD32 positive cells after exposure to IL-6. For the M1 assay, 75,000 were stimulated with 4 ng/mL IL-6 and 125 ng/mL IL-6Ra in 1:1 mix of DMEM/MEM media containing 10% FBS, 2×NEAA, 2× vitamin solution (Gibco). Inhibition was tested by the addition of varying concentrations of RDB1601 and RDB1613 and incubated for 72 hours at 37° C., 5% $CO_2$. M1 cells were then stained with an anti-mouse CD32-PE antibody (R&D Systems) and analyzed by flow cytometry.

Figure 5:
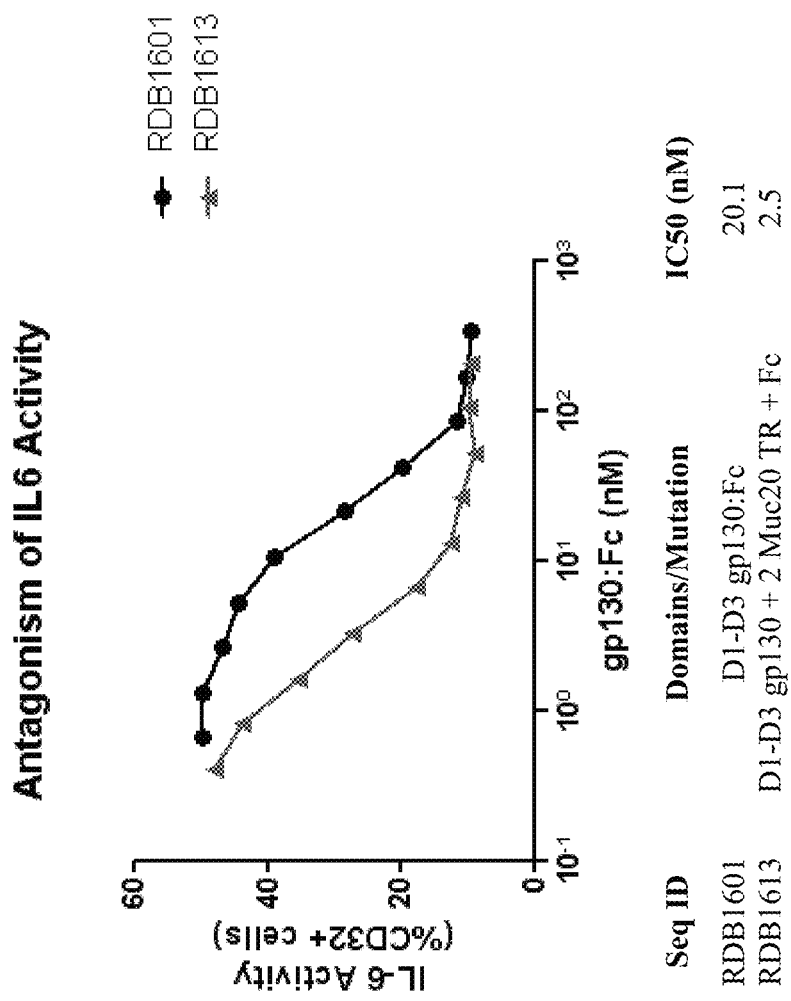
FIG. 5: Inhibition of IL-6-mediated differentiation of M1 cells RDB1601 (-●-) and RDB1613 (-▲-). Estimated values of $IC_{50}$ are reported in the table.

RDB1601 (non-mucin linker construct) inhibited IL-6-dependent differentiation of M1 cells in a dose dependent fashion with an $IC_{50}$ of 20.1 nM, whereas the mucin-containing construct RDB1613 had an $IC_{50}$ of 2.5 nM. (FIG. 5). Thus, RDB1613 is eight-fold more potent than the non-mucin linker construct RDB1601.

Example 5

Inhibition of IL-6-dependent Differentiation of M1 Cells by cpIL-6-gp130D1-mucin-(IgG2)Fc Fusion Protein RDB1562 (SEQ ID NO:19)

Fusion proteins comprising a circularly permuted IL-6 (cpIL-6), the D1 domain of human gp130 (gp130D1) and the Fc domain from IgG2 were expressed with (RDB1562, SEQ ID NO:19) and without (RDB1542, SEQ ID NO: 18) 2 tandem repeats from human MUC20 inserted between the gp130D1 domain and the Fc domain. The genes were synthesized (Geneart) and cloned into pcDNA™ (Invitrogen) and transiently expressed in CHO-S cells using FreeStyle™ MAX Reagent (Life Technologies). Proteins were purified using Protein A (GE Healthcare) and dialyzed against PBS. In vitro bioactivity was assessed by evaluating the ability of RDB1542 and RDB1562 to inhibit IL-6-dependent differentiation of M1 cells, as measured by the percent of CD32 positive cells after exposure to IL-6, as described in Example 4.

Figure 6:
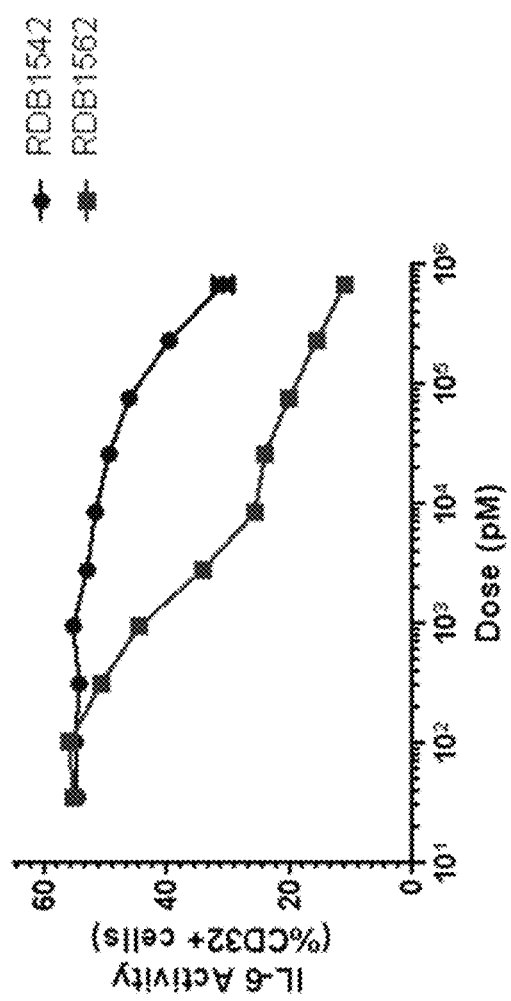
FIG. 6: Inhibition of IL-6 mediated differentiation of M1 cells by RDB1542 and RDB1562.

Both RDB1542 (the non-mucin linker construct) and RDB1562 (the mucin-containing construct) inhibited IL-6-dependent differentiation of M1 cells in a dose dependent fashion with $IC_{50}$s of >1.0 mM and 2.6 nM, respectively (FIG. 6). Thus, insertion of the mucin domain as a linker results in a molecule that is >400-fold more potent than the equivalent molecule without the mucin linker.

Example 6

Inhibition of IL-1β-dependent Signaling by IL-1Ra-mucin-(IgG2)Fc Fusion Protein RDB1840 (SEQ ID NO:21)

Fusion proteins of human IL-1Ra with the Fc domain from IgG2 were made where the IL-1Ra was either directly linked through the IgG2 hinge (RDB1841, SEQ ID NO:20) or where 2 tandem repeats from human MUC20 were inserted between the Fc domain and IL-1Ra (RDB1840, SEQ ID NO:21). The genes were synthesized (Geneart) and cloned into pcDNA™ (Invitrogen) and transiently expressed in CHO-S cells using FreeStyle™ MAX Reagent (Life Technologies). Proteins were purified using Protein A (GE Healthcare) and dialyzed against PBS. In vitro bioactivity was assessed by evaluating the ability of RDB1840 and RDB1841 to inhibit IL-1β-dependent signaling in HEK-Blue™ IL-1β cells (InvivoGen), as described in Example 1.

Figure 7:
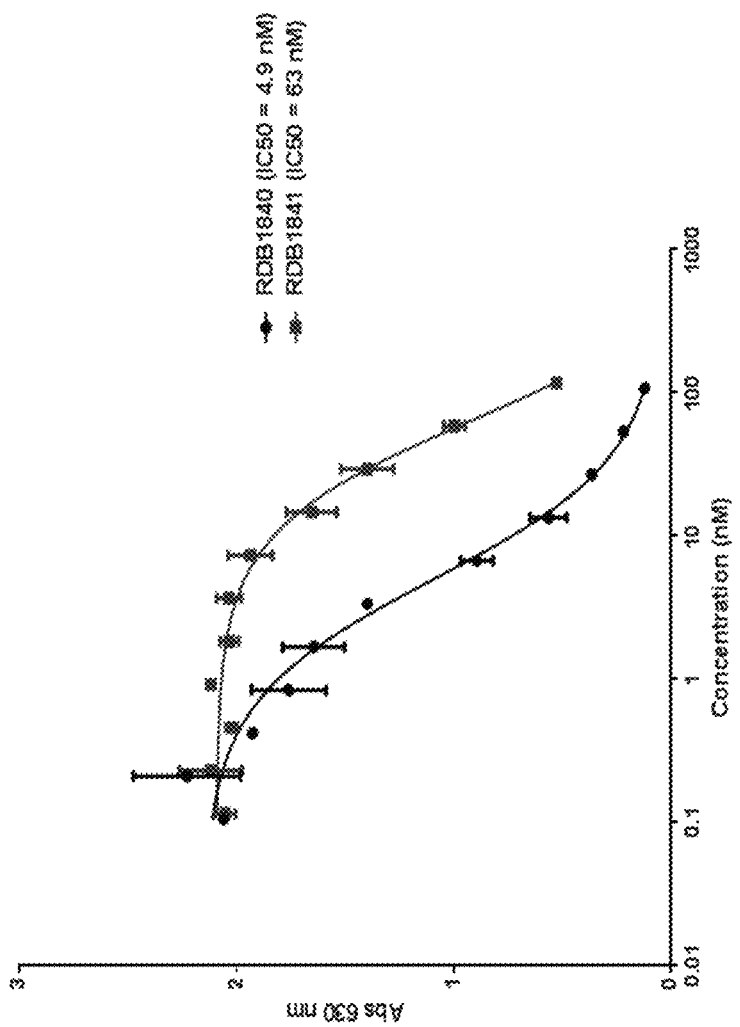
FIG. 7: IL-1β-dependent signaling in HEK-Blue™ IL-1β cells by RDB1840 and RDB1841.

Both RDB1841 and RDB1840 inhibited IL-1β-dependent signaling in a dose dependent fashion. RDB1840, containing the mucin linker, inhibited signaling with about 12-fold greater potency ($IC_{50}$ of 5.0 nM) than RDB1841, lacking the mucin linker, ($IC_{50}$ of 63.0 nM) (FIG. 7).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

---

SEQUENCE LISTING

1)
PRT
>RDB1800 (SEQ. ID. NO. 1)
1
MDAMKRGLCCVLLLCGAVFVSARRPSGRKSSKMQAFRIWDVNQKTFYLR
NNQLVAGYLQGPNVNLEEKID
VVPIEPHALFLGIHGGKMCLSCVKSGDETRLQLEAVNITDLSENRKQDK
RFAFIRSDSGPTTSFESAACP
GWFLCTAMEADQPVSLTNMPDEGVMVTKFYFQEDETGGGTHTCPPCPAP
ELLGGPSVFLFPPKPKDTLMI
SRTPEVTCVVVDVSHEDPEVKFNWYVDGVEVHNAKTKPREEQYNSTYRV
VSVLTVLHQDWLNGKEYKCKV
SNKALPAPIEKTISKAKGQPREPQVYTLPPSREEMTKNQVSLTCLVKGF
YPSDIAVEWESNGQPENNYKT

SEQUENCE LISTING

```
TPPVLDSDGSFFLYSKLTVDKSRWQQGNVFSCSVMHEALHNHYTQKSLS
LSPGK

2)
PRT
>RDB1819 (SEQ. ID. NO. 2)
1
MDAMKRGLCCVLLLCGAVFVSARRPSGRKSSKMQAFRIWDVNQKTFYLR
NNQLVAGYLQGPNVNLEEKID
VVPIEPHALFLGIHGGKMCLSCVKSGDETRLQLEAVNITDLSENRKQDK
RFAFIRSDSGPTTSFESAACP
GWFLCTAMEADQPVSLTNMPDEGVMVTKFYFQEDESGSGGASSESSASS
DGPHPVITESRASSESSASSD
GPHPVITESREPKSSDKTHTCPPCPAPELLGGPSVFLFPPKPKDTLMIS
RTPEVTCVVVDVSHEDPEVKF
NWYVDGVEVHNAKTKPREEQYNSTYRVVSVLTVLHQDWLNGKEYKCKVS
NKALPAPIEKTISKAKGQPRE
PQVYTLPPSREEMTKNQVSLTCLVKGFYPSDIAVEWESNGQPENNYKTT
PPVLDSDGSFFLYSKLTVDKS
RWQQGNVFSCSVMHEALHNHYTQKSLSLSPGK

3)
PRT
>RDB1601 (SEQ. ID. NO. 3)
1
MDAMKRGLCCVLLLCGAVFVSARLLDPCGYISPESPVVQLHSNFTAVCV
LKEKCMDYFHVNANYIVWKTNHFTIPKEQYTIINRTASSVTFTDIASLN
IQLTCNILTFGQLEQNVYGITIISGLPPEKPKNLSCIVNEGKKMRCEWD
GGRETHLETNFTLKSEWATHKFADCKAKRDTPTSCTVDYSTVYFVNIEV
WVEAENALGKVTSDHINFDPVYKVKPNPPHNLSVINSEELSSILKLTWT
NPSIKSVIILKYNIQYRTKDASTWSQIPPEDTASTRSSFTVQDLKPFTE
YVFRIRCMKEDGKGYWSDWSEEASGITTGGGPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGK

4)
PRT
>RDB1613 (SEQ. ID. NO. 4)
1
MYRMQLLSCIALSLALVTNSLLDPCGYISPESPVVQLHSNFTAVCVLKE
KCMDYFHVNANYIVWKTNHFTIPKEQYTIINRTASSVTFTDIASLNIQL
TCNILTFGQLEQNVYGITIISGLPPEKPKNLSCIVNEGKKMRCEWDGGR
ETHLETNFTLKSEWATHKFADCKAKRDTPTSCTVDYSTVYFVNIEVWVE
AENALGKVTSDHINFDPVYKVKPNPPHNLSVINSEELSSILKLTWTNPS
IKSVIILKYNIQYRTKDASTWSQIPPEDTASTRSSFTVQDLKPFTEYVF
RIRCMKEDGKGYWSDWSEEASGITYEDRGGGSGGGASSESSASSDGPHP
VITESRASSESSASSDGPHPVITESREPKSSDKTHTCPPCPAPELLGGP
SVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHN
HYTQKSLSLSPGK

5)
PRT
MUC1 tandem repeat unit (multiple variants)
1
PAPGSTAPPA HGVTSAPDTR

6)
PRT
MUC2 tandem repeat unit
1
ITTTTTVTPT PTPTGTQTPT TTP

7)
PRT
MUC3(A) tandem repeat unit (degenerate sequence)
1
ITTTETTSHD TPSFTSS

8)
PRT
MUC4 tandem repeat unit (degenerate sequence)
1
ATPLPVTDTS SASTGH

9)
PRT
MUC5AC tandem repeat unit
1
TTSTTSAP

10)
PRT
MUC5B tandem repeat unit (degenerate sequence)
1
ATGSTATPSS TPGTTHTPPV LTTTATTPT 11)
PRT
MUC7 tandem repeat unit (degenerate sequence)
1
TTAAPPTPSA TTQAPPSSSA PPE 12)
PRT
MUC11/12 tandem repeat unit
1
EESTTVHSSP GATGTALFP 13)
PRT
MUC17 tandem repeat unit (degenerate sequence)
1
SSSPTPAEGT SMPTSTYSEG RTPLTSMPVS TTLVATSAI
STLSTTPVDT STPVTNSTEA 14)
PRT
MUC20 tandem repeat unit
1
SESSASSDGP HPVITPSRA 15)
PRT
MUC21 tandem repeat unit (degenerate sequence)
1
ATNSESSTVS SGIST 16)
PRT
TIM-1 tandem repeat unit (degenerate sequence)
1
VPTTTT 17)
PRT
PSGL-1 tandem repeat unit (degenerate sequence)
1
QTTQPAATEA 18)
PRT
RDB1542
1
QNQWLQDMTTHLILRSFKEFLQSSLRALRQMSGGSGGGSSERIDKQIRY
ILDGISALRKETCNKSNMCESSKEALAENNLNLPKMAEKDGCFQSGFNE
ETCLVKIITGLLEFEVYLEYLQNRFESSEEQARAVQMSTKVLIQFLQKK
AKNLDAITTPDPTTNASLLTKLQASELLDPCGYISPESPVVQLHSNFTA
VCVLKEKCMDYFHVNANYIVWKTNHFTIPKEQYTIINRTASSVTFTDIA
SLNIQLTCNILTFGQLEQNVYGITIISGGSERKCCVECPPCPAPPVAGP
SVFLFPPKPKDTLMISRTPEVTCVVVDVSHEDPEVQFNWYVDGVEVHNA
KTKPREEQFNSTFRVVSVLTVVHQDWLNGKEYKCKVSNKGLPAPIEKTI
SKTKGQPREPQVYTLPPSREEMTKNQVSLTCLVKGFYPSDISVEWESNG
QPENNYKTTPPMLDSDGSFFLYSKLTVDKSRWQQGNVFSCSVMHEALHN
HYTQKSLSLSPGK
```

SEQUENCE LISTING

19)
PRT
RDB1562
1
QNQWLQDMTTHLILRSFKEFLQSSLRALRQMSGGSGGGSSERIDKQIRY
ILDGISALRKETCNKSNMCESSKEALAENNLNLPKMAEKDGCFQSGFNE
ETCLVKIITGLLEFEVYLEYLQNRFESSEEQARAVQMSTKVLIQFLQKK
AKNLDAITTPDPTTNASLLTKLQASELLDPCGYISPESPVVQLHSNFTA
VCVLKEKCMDYFHVNANYIVWKTNHFTIPKEQYTIINRTASSVTFTDIA
SLNIQLTCNILTFGQLEQNVYGITIISGGGGGSASSESSASSDGPHPVI
TESRASSESSASSDGPHPVITESRSERKCCVECPPCPAPPVAGPSVFLF
PPKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTKG
QPREPQVYTLPPSREEMTKNQVSLTCLVKGFYPSDISVEWESNGQPENN
YKTTPPMLDSDGSFFLYSKLTVDKSRWQQGNVFSCSVMHEALHNHYTQK
SLSLSPGK

20)
PRT
RDB1841
1
RPSGRKSSKMQAFRIWDVNQKTFYLRNNQLVAGYLQGPNVNLEEKIDVV
PIEPHALFLGIHGGKMCLSCVKSGDETRLQLEAVNITDLSENRKQDKRF
AFIRSDSGPTTSFESAACPGWFLCTAMEADQPVSLTNMPDEGVMVTKFY
FQEDEERKCCVECPPCPAPPVAGPSVFLFPPKPKDTLMISRTPEVTCVV
VDVSHEDPEVQFNWYVDGVEVHNAKTKPREEQFNSTFRVVSVLTVVHQD
WLNGKEYKCKVSNKGLPAPIEKTISKTKGQPREPQVYTLPPSREEMTKN
QVSLTCLVKGFYPSDISVEWESNGQPENNYKTTPPMLDSDGSFFLYSKL
TVDKSRWQQGNVFSCSVMHEALHNHYTQKSLSLSPGK

21)
PRT
RDB1840
1
RPSGRKSSKMQAFRIWDVNQKTFYLRNNQLVAGYLQGPNVNLEEKIDVV
PIEPHALFLGIHGGKMCLSCVKSGDETRLQLEAVNITDLSENRKQDKRF
AFIRSDSGPTTSFESAACPGWFLCTAMEADQPVSLTNMPDEGVMVTKFY
FQEDESGSGGASSESSASSDGPHPVITESRASSESSASSDGPHPVITES
RERKCCVECPPCPAPPVAGPSVFLFPPKPKDTLMISRTPEVCVVVDVS
HEDPEVQFNWYVDGVEVHNAKTKPREEQFNSTFRVVSVLTVVHQDWLNG
KEYKCKVSNKGLPAPIEKTISKTKGQPREPQVYTLPPSREEMTKNQVSL
TCLVKGFYPSDISVEWESNGQPENNYKTTPPMLDSDGSFFLYSKLTVDK
SRWQQGNVFSCSVMHEALHNHYTQKSLSLSPGK

What is claimed is:

1. A fusion protein comprising amino acids 24-452 of SEQ ID NO: 2 or an amino acid sequence homologous to amino acids 24-452 of SEQ ID NO: 2 with at least 98% amino acid sequence identity over the entire length of amino acids 24-452 of SEQ ID NO: 2 and having the receptor antagonist activity of amino acids 24-452 of SEQ ID NO: 2.

2. A fusion protein comprising amino acids 24-452 of SEQ ID NO: 2.

3. A composition comprising the fusion protein of claim 1 and at least one pharmaceutically acceptable carrier.

4. A composition comprising the fusion protein of claim 2 and at least one pharmaceutically acceptable carrier.

5. The fusion protein of claim 1, wherein the fusion protein is glycosylated.

6. The fusion protein of claim 2, wherein the fusion protein is glycosylated.

7. A fusion protein comprising a first fusion partner that is linked to a second fusion partner by a mucin domain polypeptide linker, wherein the first fusion partner is IL-1Ra or a protein having at least 98% amino acid sequence identity to IL-1Ra and having the receptor antagonist activity of IL-Ra, and wherein the second fusion partner comprises all or a portion of an immunoglobulin comprising an Fc region, wherein the mucin domain polypeptide linker comprises SEQ ID NO: 14 or an amino acid sequence having at least 90% sequence identity to SEQ ID NO: 14 and wherein the half-life of the fusion protein is improved as compared to a fusion of the first fusion partner to the second fusion partner in the absence of the mucin domain polypeptide linker.

* * * * *